(12) United States Patent
Nagakubo et al.

(10) Patent No.: US 8,853,648 B2
(45) Date of Patent: Oct. 7, 2014

(54) SAMPLE HOLDER, METHOD FOR USE OF THE SAMPLE HOLDER, AND CHARGED PARTICLE DEVICE

(75) Inventors: Yasuhira Nagakubo, Hitachinaka (JP); Toshiaki Tanigaki, Hitachinaka (JP); Katsuji Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 133 days.

(21) Appl. No.: 13/264,933

(22) PCT Filed: Apr. 7, 2010

(86) PCT No.: PCT/JP2010/002525
§ 371 (c)(1),
(2), (4) Date: Jan. 3, 2012

(87) PCT Pub. No.: WO2010/122717
PCT Pub. Date: Oct. 28, 2010

(65) Prior Publication Data
US 2012/0112064 A1      May 10, 2012

(30) Foreign Application Priority Data
Apr. 22, 2009   (JP) .................................. 2009-103518

(51) Int. Cl.
*H01J 37/20*    (2006.01)
*G01N 1/28*     (2006.01)

(52) U.S. Cl.
CPC ......... *H01J 37/20* (2013.01); *H01J 2237/2001* (2013.01); *H01J 2237/31745* (2013.01); *H01J 2237/20214* (2013.01); *H01J 2237/31749* (2013.01); *H01J 2237/2802* (2013.01); *H01J 2237/2065* (2013.01); *G01N 1/286* (2013.01)
USPC ..................... 250/443.1; 250/442.11; 250/307

(58) Field of Classification Search
CPC .................................. H01J 37/20; G21K 7/00
USPC ........................ 250/443.1, 442.11, 307, 491.1
See application file for complete search history.

(56) References Cited

U.S. PATENT DOCUMENTS 3,643,091 A * 2/1972 Lucas ....................... 250/442.11
4,703,181 A * 10/1987 Swann et al. ............ 250/442.11
(Continued)

FOREIGN PATENT DOCUMENTS

DE   698 16 974 T2   7/2004
JP     2774884 B2    4/1998
(Continued)

OTHER PUBLICATIONS

Japanese Office Action issued in Japanese Patent Application No. 2009-103518 mailed Oct. 2, 2012.
(Continued)

*Primary Examiner* — Jack Berman
*Assistant Examiner* — Wyatt Stoffa
(74) *Attorney, Agent, or Firm* — McDermott Will & Emery LLP

(57) ABSTRACT

A sample holder for efficiently performing the processing or observation of a sample by means of charged particles while cooling. Particularly, disclosed is a sample holder whereby the processing or observation of a material which may be affected by the influence of heat damage can be performed in a state in which the material is cooled, and furthermore, the influence due to a sample processing method using charged particles can be reduced by cooling. The sample holder is provided with a sample stage capable of fixing a sample piece extracted from a sample by ion beam irradiation, and a rotation mechanism for rotating the sample stage in a desired direction, which can be attached to an ion beam device and a transmission electron microscope device, and which has a movable heat transfer material for thermally connecting the sample stage and a cooling source, and an isolation material for thermally isolating the sample stage and the heat transfer material from the outside. According to the sample holder, the processing or observation of a sample by means of charged particle beams can be performed while efficiently cooling.

12 Claims, 14 Drawing Sheets

(56) References Cited

U.S. PATENT DOCUMENTS

| | | | |
|---|---|---|---|
| 4,833,330 A * | 5/1989 | Swann et al. | 250/443.1 |
| 4,950,901 A * | 8/1990 | Jones et al. | 250/443.1 |
| 5,104,694 A * | 4/1992 | Saito et al. | 427/255.18 |
| 5,225,683 A * | 7/1993 | Suzuki et al. | 250/442.11 |
| 5,744,800 A * | 4/1998 | Kakibayashi et al. | 250/311 |
| 5,753,924 A * | 5/1998 | Swann | 250/443.1 |
| 5,898,177 A * | 4/1999 | Hidaka et al. | 250/311 |
| 5,986,270 A * | 11/1999 | Bormans et al. | 250/442.11 |
| 6,388,262 B1 * | 5/2002 | Alani et al. | 250/442.11 |
| 6,410,925 B1 * | 6/2002 | Armbruster et al. | 250/442.11 |
| 6,414,323 B1 * | 7/2002 | Abe et al. | 250/443.1 |
| 6,444,982 B1 * | 9/2002 | Mitchell et al. | 250/311 |
| 6,495,838 B1 * | 12/2002 | Yaguchi et al. | 250/443.1 |
| 7,238,953 B2 * | 7/2007 | Zandbergen | 250/440.11 |
| 7,420,184 B2 * | 9/2008 | van de Water et al. | 250/442.11 |
| 7,644,637 B2 * | 1/2010 | Moore et al. | 73/863 |
| 8,497,487 B2 * | 7/2013 | Milas et al. | 250/440.11 |
| 2002/0005492 A1 * | 1/2002 | Hashikawa et al. | 250/442.11 |
| 2006/0097187 A1 * | 5/2006 | Zandbergen | 250/440.11 |
| 2008/0173813 A1 * | 7/2008 | Van De Water et al. | 250/307 |
| 2008/0283750 A1 * | 11/2008 | Nakazawa et al. | 250/311 |
| 2010/0006771 A1 * | 1/2010 | Miyazaki | 250/442.11 |
| 2011/0115637 A1 * | 5/2011 | Kikuchi et al. | 340/600 |
| 2012/0024086 A1 * | 2/2012 | Stabacinskiene et al. | 73/864.91 |

FOREIGN PATENT DOCUMENTS

| | | |
|---|---|---|
| JP | 10-275582 A | 10/1998 |
| JP | 11-096953 A | 4/1999 |
| JP | 2000-513135 A | 10/2000 |
| JP | 2001-066231 A | 3/2001 |
| JP | 2001-066231 A | 3/2001 |
| JP | 2002-025490 A | 1/2002 |
| JP | 2002-025490 A | 1/2002 |
| JP | 2002-134059 A | 5/2002 |
| JP | 2002-134059 A | 5/2002 |
| JP | 2004-508661 A | 3/2004 |
| JP | 2004-508661 A | 3/2004 |
| JP | 2006-313704 A | 11/2006 |
| JP | 2006-313704 A | 11/2006 |
| JP | 2008-508684 A | 2/2008 |
| JP | 2008-508684 A | 3/2008 |

OTHER PUBLICATIONS

Ohnishi et al., "A New Focused-Ion-Beam Microsampling Technique for TEM Observation of Site-specific Areas," *Proc 25th Int Symp Test and Fail Anal*, (2009), pp. 449-453.

Ziegler, "Particle Interactions with Matter," Searched Apr. 13, 2009, http://www.srim.org.

German Office Action, w/ English translation thereof, issued in German Patent Application No. 11 2010 001 712.3 dated Feb. 1, 2013.

M.R. Rudman et al., "A simple design for a low temperature electron microscope stage," Micron 3 (1972), 396-405.

H.G. Heide, "Principles of a TEM Specimen Device to Meet Highest Requirements: Specimen Temperature 5-300 K, Cryo Transfer, Condensation Protection, Specimen Tilt, Stage Stability for High Resolution," Ultramicroscopy 6 (1981), 115-124.

* cited by examiner

FIG.1
(a)
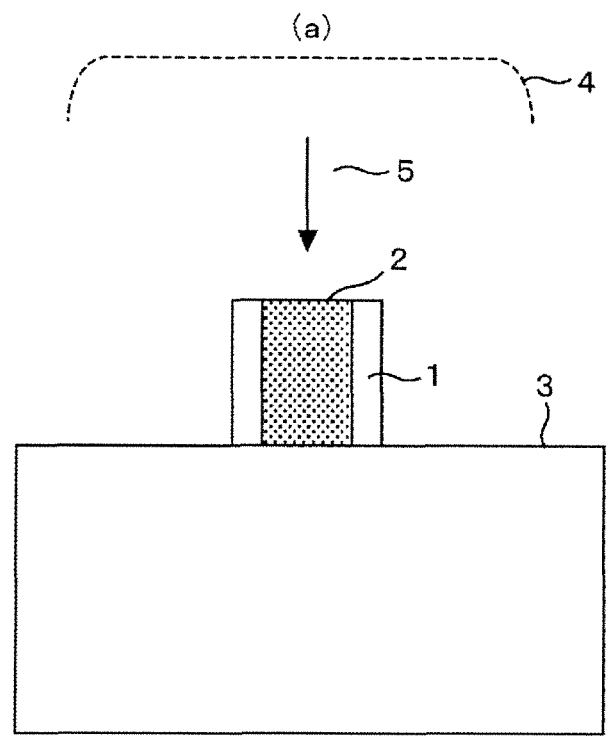
(b)
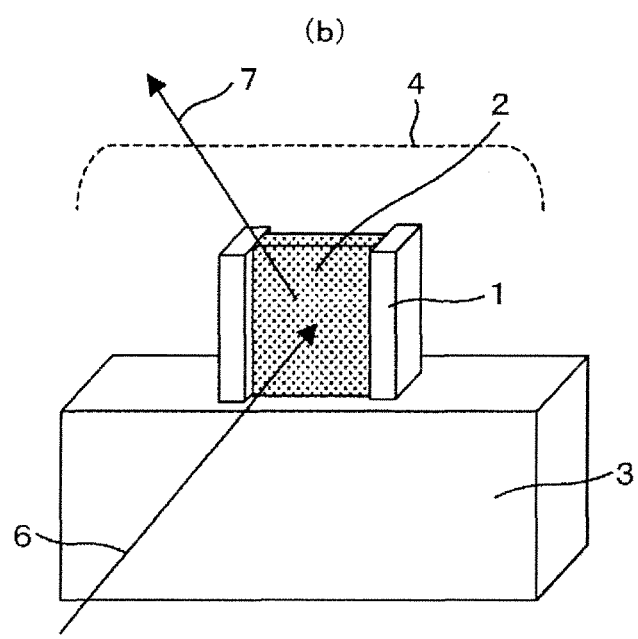

FIG.4
(a)
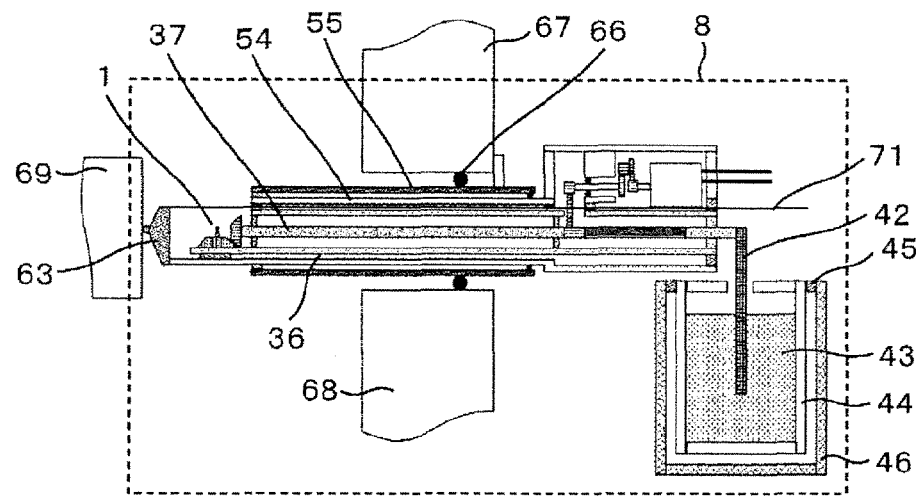
(b)
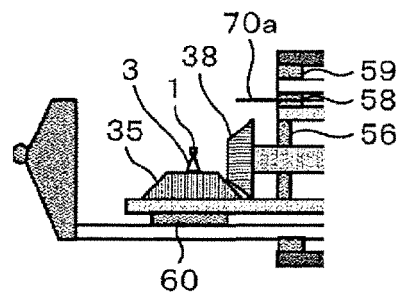
(c)
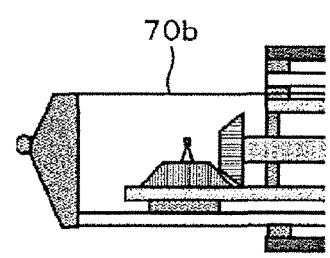
(d)
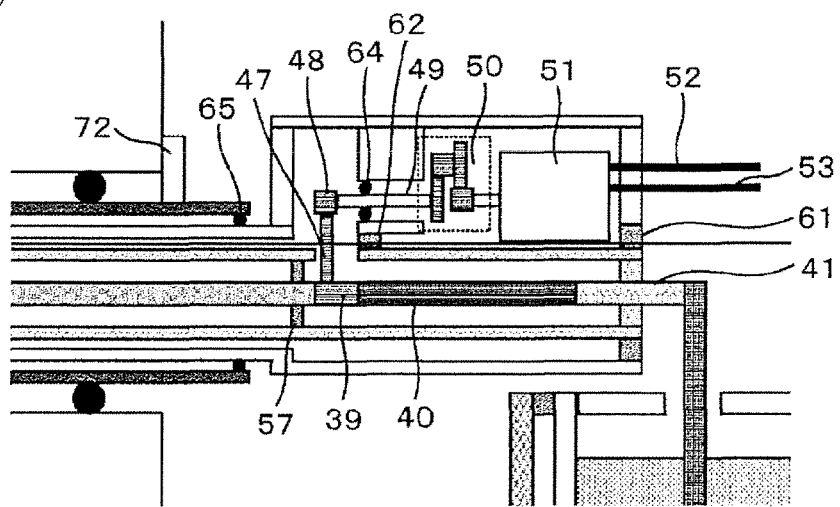

FIG.5
(a)
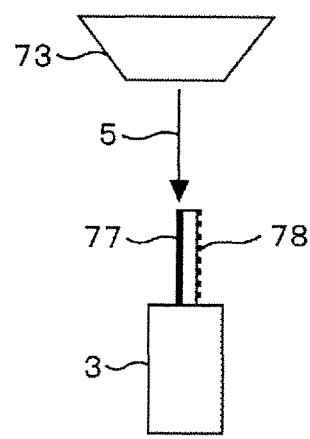
(b)
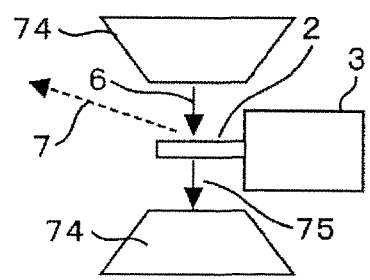
(c)
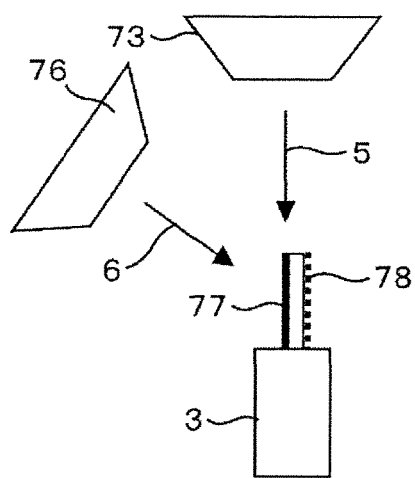
(d)
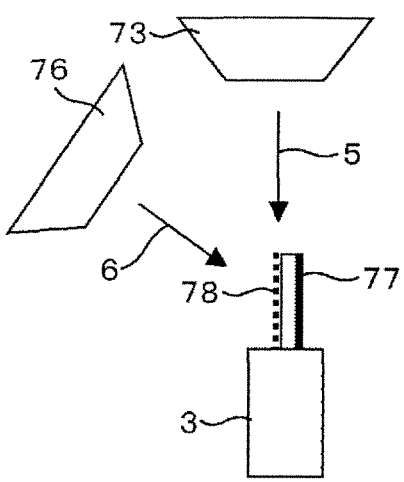
(e)
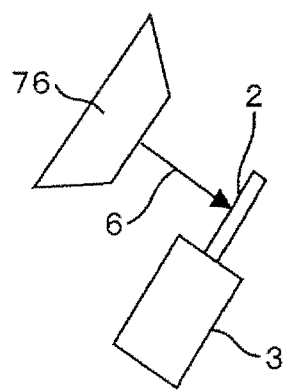

FIG.7
(a)
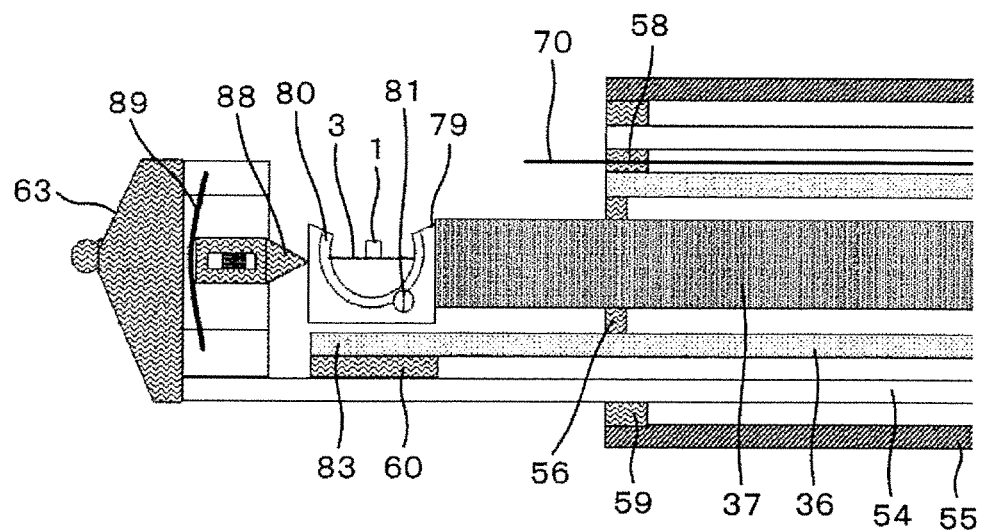
(b)
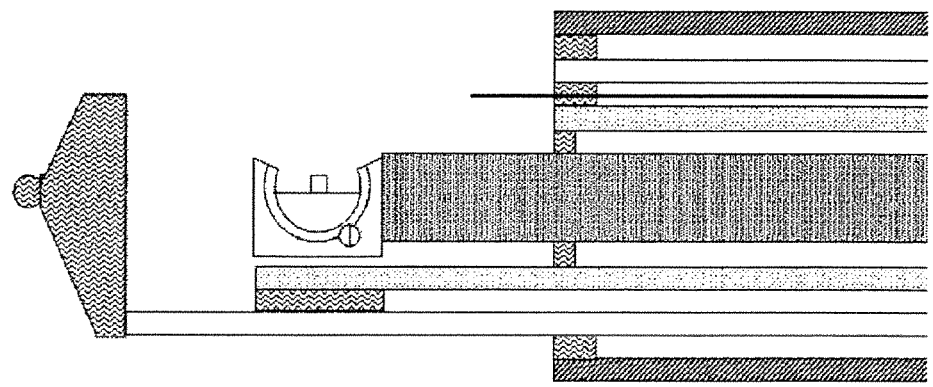

FIG.11
(a)
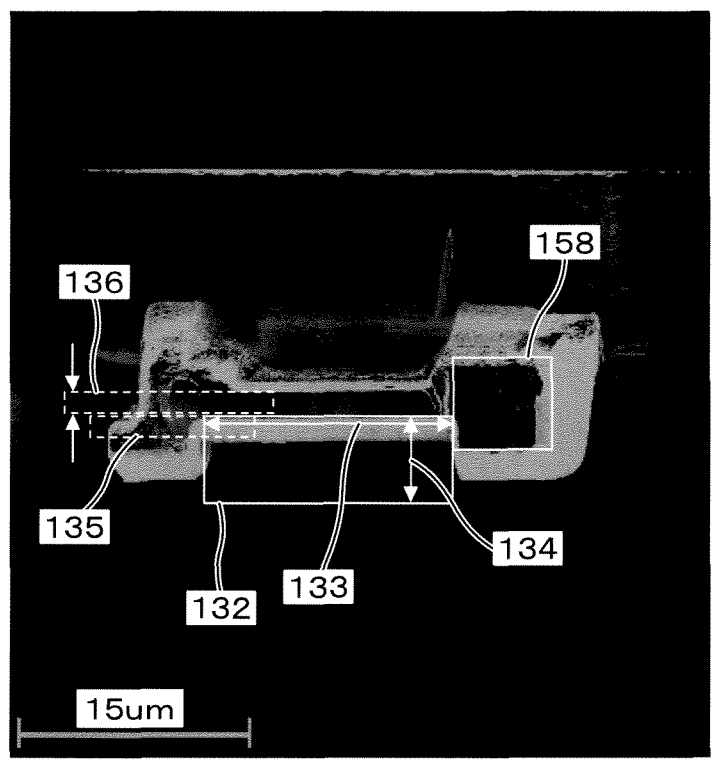
(b)
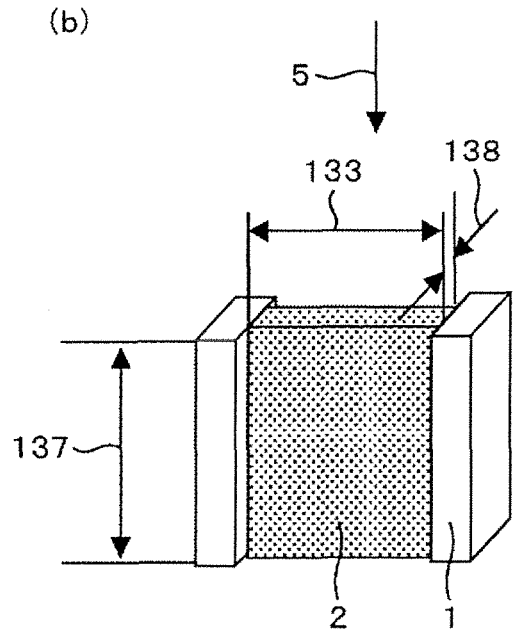
(c)
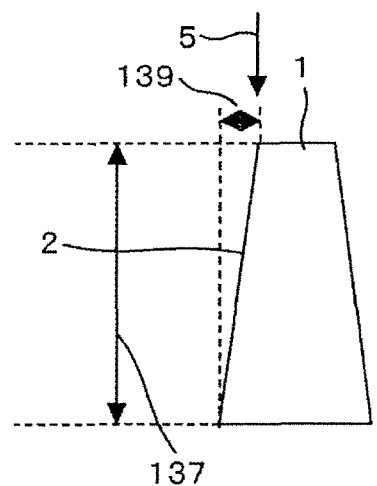

FIG.14
(a)
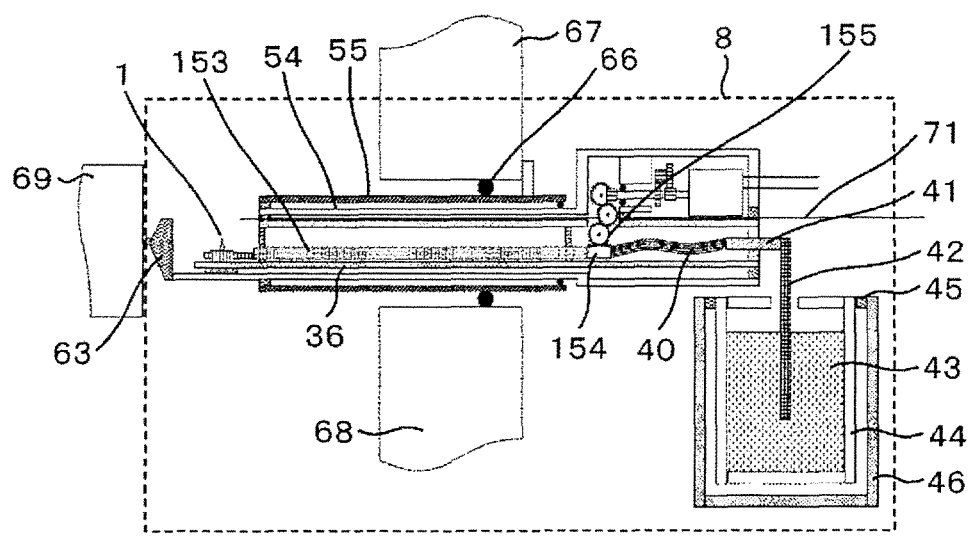
(b)
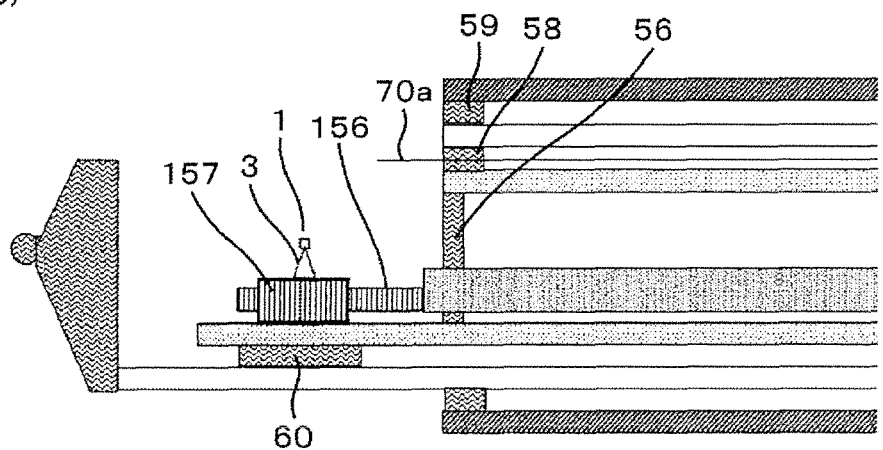

SAMPLE HOLDER, METHOD FOR USE OF THE SAMPLE HOLDER, AND CHARGED PARTICLE DEVICE

RELATED APPLICATIONS

This application is the U.S. National Phase under 35 U.S.C. §371 of International Application No. PCT/JP2010/002525, filed on Apr. 7, 2010, which in turn claims the benefit of Japanese Application No. 2009-103518, filed on Apr. 22, 2009, the disclosures of which Applications are incorporated by reference herein.

TECHNICAL FIELD

The present invention relates to a manufacturing of a sample for a transmission electron microscope by a charged particle device, for example, a focused ion beam processing and observing device (FIB).

BACKGROUND ART

The FIB is a device which can process a material in an optical shape while utilizing a sputtering effect, by focusing a charged particle so as to irradiate onto a sample. Further, the FIB can pick up an optical place from a target position.

A method disclosed in JP-B2-2774884 (patent document 1) is called as an FIB micro sampling method. The FIB micro sampling method is a most suitable sample manufacturing method at a time of carrying out an analysis of a state and a structure of several nm order corresponding to a subject of research of a nanotechnology in recent years by means of an electron microscope or the like.

On the other hand, in the case of observing a manufactured thin film sample by the electron microscope, a temperature of the sample rises up under the influence of an electron beam, and there is a case that it is hard to analyze original aspect and state of the sample. With respect to the problem, in JP-A-11-96953 (patent document 2), there is proposed a method of observing a sample while cooling.

PRIOR ART DOCUMENT

Patent Document

Patent Document 1: JP-B2-2774884
Patent Document 2: JP-A-11-96953
Patent Document 3: JP-A-10-275582
Patent Document 4: U.S. Pat. No. 5,986,270
Patent Document 5: JP-A-2000-513135
Patent Document 6: JP-A-2004-508661

Non-Patent Document

Non-Patent Document 1: Ohnishi T., Koike H., Ishitani T., Tomimatsu S., Umemura K., and Kamino T., Proc. 25th Int. Symp. Test. And Fail. Anal. (1999) 449-453.
Non-Patent Document 2: James F. Ziegler, "The Stopping and Range of Ions in Matter", [online], [searched on Apr. 13, 2009], Internet (http://www.srim.org)

SUMMARY OF THE INVENTION

Problem to be Solved by the Invention

As a result of devoting himself to make a study of manufacturing of a sample for a transmission electron microscope by the inventor of the present application, the following knowledge has found.

Even in the process using the charged particle such as the FIB, the rising of the sample temperature occurs in some condition. It is thought to be effective to process the sample while cooling, with respect to a resin, a low-melting metal, a low-temperature phase change material and the like which have a weakness for a heat. However, there is a case that a target cooling temperature can not be obtained in some condition for processing. In the process of the charged particle, a charged particle having an energy comes into collision with a sample processing position, and a part of the energy is used partly for sputtering, however, the remaining energy is taken in the sample and is converted into a heat energy. The heat energy is transferred within the sample and is diffused to a cooling position, thereby settling down a temperature in the vicinity of a cooling temperature after a fixed time. However, in the case that the heat energy which the irradiation of the charged particle gives goes beyond a heat transfer amount heading for the cooling portion, the temperature rise of the sample is generated. As a result, the process by the charged particle while cooling requires an appropriate regulation of the cooling temperature and the charged particle irradiation condition while taking into consideration a heat transfer characteristic of the sample and the sample aspect.

Further, in many of the samples exposed to a thermal damage, a coefficient of thermal conductivity of the sample itself is low. With regard to the observation of the electron beam, a charge up of the sample and the heat transfer characteristic greatly contribute to the thermal damage. There is desired a method of processing and observing the sample having the low coefficient of thermal conductivity while efficiently cooling.

A technique disclosed in the patent document 2 is a system for cooling by installing a cooling portion which enwraps a sample in a holder. In accordance with this, even if a composition analysis of the sample is intended to be carried out by an energy dispersion type X-ray analysis (EDX), the X-ray emitted from the sample does not reach a detector. As a result, it is hard to use a holder with a cooling mechanism so as to carry out the EDX analysis. Further, the holder with the cooling mechanism can barely cool, and a freedom of angle of rotation is limited in some magnitudes of a cooling system. A biaxial inclination is necessary in the observation of a crystalline sample, however, a biaxial observation while cooling is hard.

In the method of cold processing and observing, it is necessary to reload the sample in the case that a working device and an observing device are different, and the case that the holders are different. Since the sample for the electron microscope observation is a thin segmented micro piece, a meticulous care is required for handling. Therefore, there is desired a holder which can carry out from a sample manufacturing to an observation as it is.

Further, in accordance with an evolution of a nanotechnology in recent years, the necessity for manufacturing a refined specified region as a sample on the basis of the FIB process has been enhanced. In the case mentioned above, there is employed a step of bringing forward the FIB process while interrupting the FIB process and determining the processing condition by an electron microscope. Even in this case, it is useful that the processing holder and the observing holder are in common. If the sample is reloaded for processing and observing each time, a final processing time becomes long.

Further, in the case of the FIB process while cooling, if a worker reloads the sample by a manual labor, the sample is once exposed to the ambient air. Generally, if the cooling material is exposed to the ambient air, a dew condensation is generated, and the sample surface is covered by innumerable ices. Accordingly, it is impossible to make the cooling material be exposed to the ambient air as it is. In order to avoid the dew condensation, it is necessary to temporarily turn back the sample temperature to the room temperature from a state of cooling and processing, and thereafter being exposed to the ambient air. Further, it is necessary to again cool for cooling and observing after reloading on the observing holder by a manual labor. In this case, a lot of time is required, and in the case that an additional process is necessary after the observation, it is necessary to again turn back the sample to the room temperature, reload on the processing holder by a manual labor and cool for processing. A tire for cooling and a time for turning back to the room temperature are both between 15 and 30 minutes. The smaller the observed position is, the more a confirmation work by the processing and the observing is. Accordingly, series of working time in the cooling FIB process becomes enormous. The reloading work of the sample is a process which is most worried about in the cooling FIB process. In the cooling FIB process, it is desirable that the processing holder and the observing holder are the same.

However, in the meantime, there is a case that it is desirable to manufacture a plurality of samples and observe them collectively later. For that purpose, a sample table which can be detached from the holder is necessary. In this case, conventionally, a mesh for the electron microscope fulfills the role, and it is necessary to manufacture and keep the mesh as occasion demands. In other words, there is demanded a processing and observing system which is structured such that the processing holder and the observing holder are the same, can equip the sample table which can be detached, and has the cooling mechanism.

Further, even in the case that the processing and observing by the different charged particles come and go, there is an appropriate sample direction in correspondence to each of the purposes. For example, it is necessary to process while irradiating an ion beam on a thin film surface from a parallel direction in the FIB, and it is necessary that the electron beams are irradiated vertically to the thin film surface in the observation by the electron microscope. In the case of coming and going between the processing and observing by the different charged particles, a mechanism for rotating the direction of the sample at about 180 degree is demanded.

An object of the present invention relates to efficiently carry out a processing or an observing by a charged particle while cooling. Particularly, it relates to process and observe a material which is worried about an influence of a heat damage in a cooled state. Further, it relates to effectively reduce an influence given by a sample processing method using a charged particle by cooling.

Means for Solving the Problem

The present invention relates to a sample holder which is provided with a sample table to which a sample piece picked out of a sample in accordance with an ion beam irradiation can be fixed, and a rotation mechanism which rotates the sample table in a desired direction, can be installed to an ion beam device and a transmission electron microscope, and has a movable heat transfer material which thermally connects the sample table and a cooling source, and an isolation material thermally isolating the sample table and the heat transfer material from an outer world.

Effect of the Invention

In accordance with the present invention, it is possible to carry out a processing and an observing by a charged particle ray while efficiently cooling.

BRIEF DESCRIPTION OF THE DRAWINGS

FIGS. 1(a) and 1(b) are schematic views of a micro sample cooling sample table, in which FIG. 1(a) shows a positional relationship between a sample and a charged particle in a processing charged particle device, and FIG. 1(b) shows a positional relationship between the sample and the charged particle in an observing charged particle device;

FIGS. 4(a), 4(b), 4(c) and 4(d) are detailed views of a part of a sample stage of the charged particle device, in which FIG. 4(a) shows a whole image of a cooling holder, FIG. 4(b) shows a detailed structure of a leading end portion of the cooling holder, FIG. 4(c) shows a detailed structure of a leading end portion of the cooling holder (using a shutter), and FIG. 4(d) shows a periphery of a sample driving machine structure existing in a terminal end portion (doubling as a handle) of the cooling holder;

FIGS. 5(a), 5(b), 5(c), 5(d) and 5(e) show a positional relationship between the device and a sample, in which FIG. 5(a) shows a sample position within an FIB device, FIG. 5(b) shows a sample position within an electron microscope, FIG. 5(c) shows a sample position A which is suitable for processing within an FIB and electron microscope conjugated device, FIG. 5(d) is a sample position B which is suitable for processing within the FIB and electron microscope conjugated device, and FIG. 5(e) is a sample position which is suitable for observing within the FIB and electron microscope conjugated device.

FIGS. 7(a) and 7(b) show a mesh corresponding uniaxial inclined cooling holder, in which FIG. 7(a) shows a typical uniaxial inclined cooling holder, and FIG. 7(b) shows a particular uniaxial cooling holder with no leading end presser foot;

FIGS. 11(a), 11(b) and 11(c) are explanation views of a processing area, a sample shape and a name, in which FIG. 11(a) shows a scanning ion microscope image and an area display frame under a thin film processing by the FIB device, FIG. 11(b) is an outline view of a micro sample and an explanatory view of a name of each of portions, and FIG. 11(c) is a cross sectional outline view in the case of viewing a thin film portion from a paper surface transverse direction, and an explanatory view of a name;

FIG. 14 shows a cooling holder.

MODE FOR CARRYING OUT THE INVENTION

Figure 2:
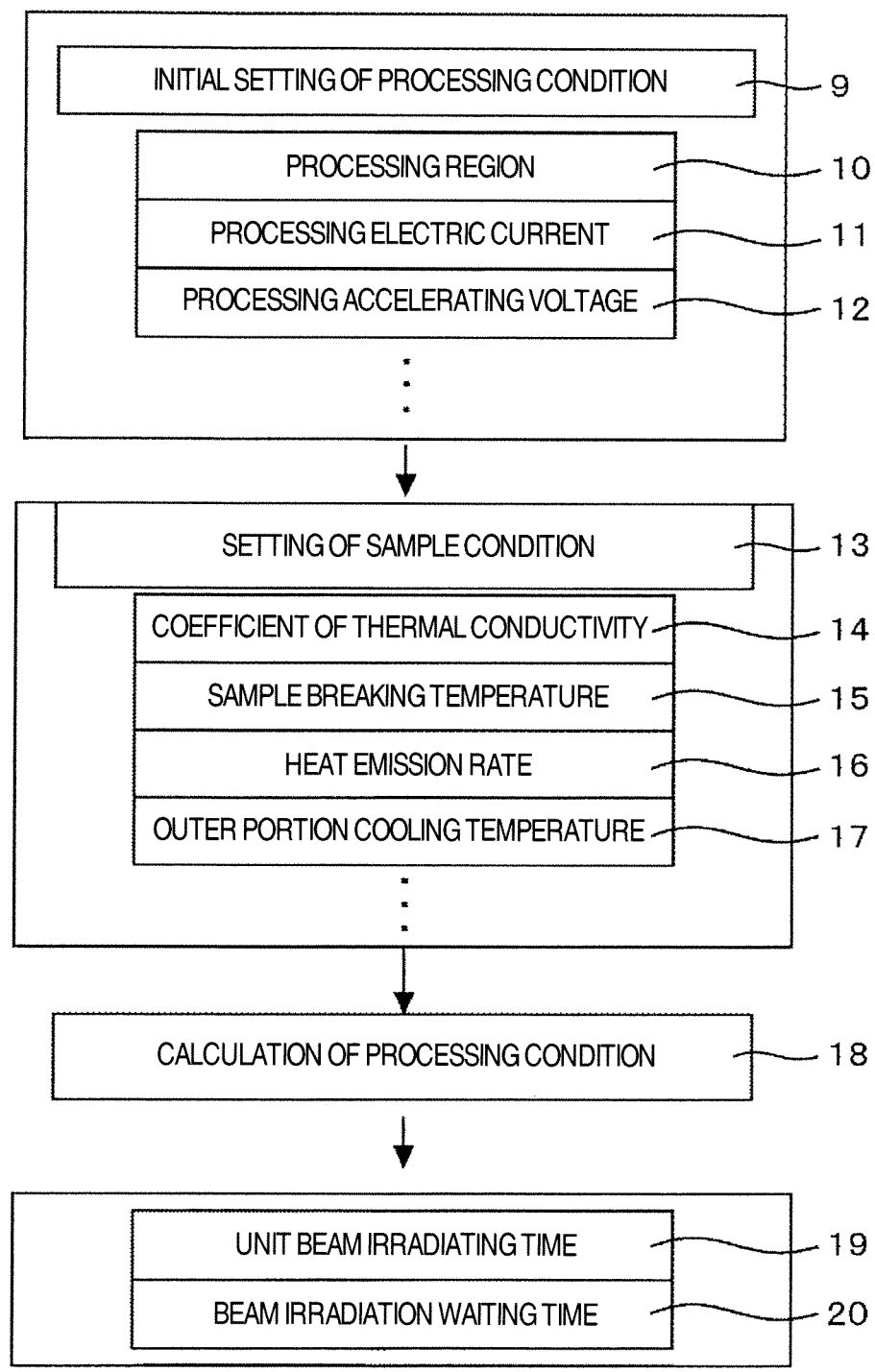
FIG. 2 is a flow chart of deciding a cooling process condition by the charged particle.

The present embodiment relates to a cooling holder which can process a sample while efficiently cooling at a time of applying a micro sampling process by a focused ion beam, and can observe a manufactured sample by an electron microscope as it is while cooling, and an FIB processing and observing device and a transmission electron microscope device which can use the cooling holder.

In the present embodiment, the micro sample is bonded directly to a cooling portion and is processed and observed by a charged particle while being efficiently cooled. The cooling portion is a sample table which can be detached. A holder holding the sample table has such a structure that can set a direction of the sample to an optimum direction for processing or observing by the different charged particles. Further, it has such a structure that can come and go between the different charged particle processing and observing device while cooling. A great space is provided in the periphery of the sample, and a structure which does not disturb a route of an ion beam and a signal (for example, a characteristic X ray or the like) generated from the sample is provided.

In the case of using the cooling holder, such a phenomenon that a coagulation material or a contamination is attached to a surface of the sample is generated in some environment within the device, the phenomenon being represented by a dew condensation. In the case that a cold finger cooled at about a temperature of a liquid nitrogen exists in the vicinity of the sample, such a problem that the coagulation material and the contamination are adsorbed by the cold finger so as to be attached to the sample can be solved. However, in the existing charged particle processing device, any similar mechanism to the cold finger is not equipped. In order to solve the problem, a micro heat transfer material is provided in a different direction from the cooling source side of the sample. In accordance with this structure, there is achieved such an arrangement that the portion cooled more than the sample exists in the vicinity of the sample within the device. This arrangement substantially serves as the cold finger, and solves such a problem that the coagulation material and the contamination are attached to the sample.

In the processing by the charged particle, an electric current amount of the charged particle, an irradiating time and a waiting time till the next irradiation are decided by taking into consideration a heat transfer characteristic of the sample, a sample aspect and a target cooling temperature, and there is carried out such a processing that does not prevent a cooling effect. Since a processing time becomes longer in the processing provided with the waiting time, a drift of the sample affects the processing. In order to solve the problem, the processing is carried out while carrying out a drift compensation.

In the embodiment, there is disclosed a sample holder which is provided with a sample table which can fix a sample piece picked out of a sample in accordance with an ion beam irradiation, and a rotation mechanism which turns the sample table in a desired direction, which can be installed to an ion beam device and a transmission electron microscope device, and which has a movable heat transfer material thermally connecting the sample table and a cooling source, and an isolation material thermally isolating the sample table and the heat transfer material from an outer world.

Further, in the embodiment, there is disclosed a sample holder in which the movable heat transfer material is a material or a structure which transfers a heat by utilizing an atomic slip phenomenon such as a plastic deformation, or utilizing a slip between the materials.

Further, in the embodiment, there is discloses a sample holder in which the movable heat transfer material has such a freedom as to turn on an axial in a holder longitudinal direction.

Further, in the embodiment, there is disclosed a sample holder in which the movable heat transfer material has such freedom as to extend and contract in a holder longitudinal direction.

Further, in the embodiment, there is disclosed a sample holder in which the direction of the sample piece can be turned at 180 degree on an axis of a holder longitudinal direction.

Further, in the embodiment, there is disclosed a sample holder in which the direction of the sample piece can be turned in two different directions.

Further, in the embodiment, there is disclosed a sample holder in which a material or a mechanism for transmitting a heat in a different direction from a cooling source side cooling the sample piece is provided, a temperature distribution is generated in the vicinity of the sample piece, and a material having a lower temperature than the sample piece exists in the vicinity of the sample piece.

Further, in the embodiment, there is disclosed a sample holder in which a material or a mechanism for transmitting the heat in the different direction from the cooling source side has a heater which uses any one of a tungsten, a molybdenum and a tantalum, and electrically controls a temperature gradient.

Further, in the embodiment, there is disclosed a sample holder in which a cover capable of being moved from an outer portion of the device is provided for protecting the sample piece at a time of moving between the charged particle devices.

Further, in the embodiment, there is disclosed a method of using a sample holder, wherein the method prevents a temperature rise of a sample by setting a unit time irradiating a charged particle to the sample and a waiting time till next irradiating the same position, in a processing or an observing of the sample by the charged particle, and regulating them.

Further, in the embodiment, there is disclosed a charged particle device to which a sample holder can be installed, wherein the charged particle device can set a unit time irradiating a charged particle beam and a waiting time till next irradiating the charged particle beam to the same place, on the basis of a coefficient of thermal conductivity of the sample piece, a specific heat capacity, an emissivity, a specific gravity, an allowable temperature at which the sample piece is thermally stable, an interaction characteristic with respect to the charged particle, a shape of the sample piece, an accelerating voltage of the charged particle device, a probe electric current, an observing region, a processing region, a processing magnification, an observing magnification and/or a sample cooling temperature.

Further, in the embodiment, there is disclosed a charged particle device which can automatically calculates a unit time and a waiting time on the basis of a coefficient of thermal conductivity of the sample piece, a specific heat capacity, an emissivity, a specific gravity, an allowable temperature at which the sample piece is thermally stable, an interaction characteristic with respect to the charged particle, a shape of the sample piece, an accelerating voltage of the charged particle device, a probe electric current, an observing region, a processing region, a processing magnification, an observing magnification and/or a sample cooling temperature.

Further, in the embodiment, there is disclosed a charged particle device which is loaded with information of an accelerating voltage of the charged particle device, a probe electric current, an observing region, a processing region, a processing magnification, an observing magnification and/or a sample cooling temperature, carries out a calculation of the processing condition and the observing condition, and carries out the processing and the observing under the condition.

Further, in the embodiment, there is disclosed a charged particle device which stores a coefficient of thermal conductivity of the sample piece, a specific heat capacity, an emissivity, a specific gravity, an allowable temperature at which the sample piece is thermally stable, and/or an interaction characteristic with respect to the charged particle as a physical data of the sample piece, and reads in as occasion demands.

Further, in the embodiment, there is disclosed a charged particle device which detects a movement by a drift of the sample piece at a time of accurately processing a desired position of the sample piece, and compensates a processing position.

A description will be given below of the novel features and effects mentioned above and the other of the present invention with reference to the accompanying drawings. In this case, the drawings are exclusively used for understanding the invention, and does not restrict the scope of the right. Further, each of the embodiments can be appropriately combined, and the combined aspects will be disclosed in the present specification.

Embodiment 1

FIG. 1 shows a schematic view of a micro sample cooling sample table in the present embodiment. A micro sample 1 is a micro sample which is manufactured, for example, by an FIB micro sampling method or the like. A processing and observing region 2 is equal to or less than 10 μm square in a normal processing and observing. This micro region is provided with a space 4 for irradiating a charged particle A5 (for example, an ion beam), and the micro sample is directly bonded to a cooling sample table 3 which is connected to a cooling source so as to be cooled.

In the observation, a charged particle B6 (for example, an electron beam or the like) is irradiated to the micro sample 1 from a vertical direction, and can be observed while being cooled. In the processing and the observing, the charged particle irradiation region is the micro region, however, it is necessary to efficiently discharge a heat generated there in order to enhance a cooling efficiency. In the present embodiment, since the processing and observing region 2 is structured such as to be close to the cooling sample table 3 at a distance which is equal to or less than several μm, a cooling effect is high. A signal 7 emitted from the sample passes through the space 4 and is efficiently detected by a detector.

A mechanism which can turn the cooling sample table 3 in a vertical direction of a paper surface and a transverse direction is provided, and it is possible to process and observe in correspondence to a purpose. Further, the cooling sample table 3 has a mechanism which can be detached from a cooling holder 8. The cooling holder 8 retaining the cooling sample table 3 has such a structure that can come and go between different charged particle devices in a state of keeping cooling.

In the case of using the cooling holder 8 in a device which does not have such a mechanism as a cold finger selectively adsorbing a material which is coagulated by cooling, a micro heat transfer material intentionally transmitting a heat in a different direction from a cooling source side of the sample is provided, and a temperature gradient is formed in the vicinity of the sample. On the basis of the temperature gradient, a portion having a lower temperature than the sample is provided in the vicinity of the sample.

The processing by the charged particle follows to a flow chart shown in FIG. 2. On the basis of an initial setting 9 of a processing condition, a processing region 10, a processing electric current 11, a processing accelerating voltage 12 and the like are set. Next, on the basis of a setting 13 of a sample condition, a coefficient of thermal conductivity 14 of the sample, a sample breaking temperature 15, a thermal emission rate 16, an outer portion cooling temperature 17 and the like are set. Further, a unit beam irradiating time 19 and a beam irradiation waiting time 20 are decided by carrying out a calculation 18 of an appropriate processing condition. A charged particle current amount, the irradiating time and the waiting time till the next irradiation are decided by taking into consideration a heat transfer characteristic of the sample, a sample aspect and/or a target cooling temperature by the means mentioned above, and a processing which does not prevent a cooling effect is carried out.

Figure 3:
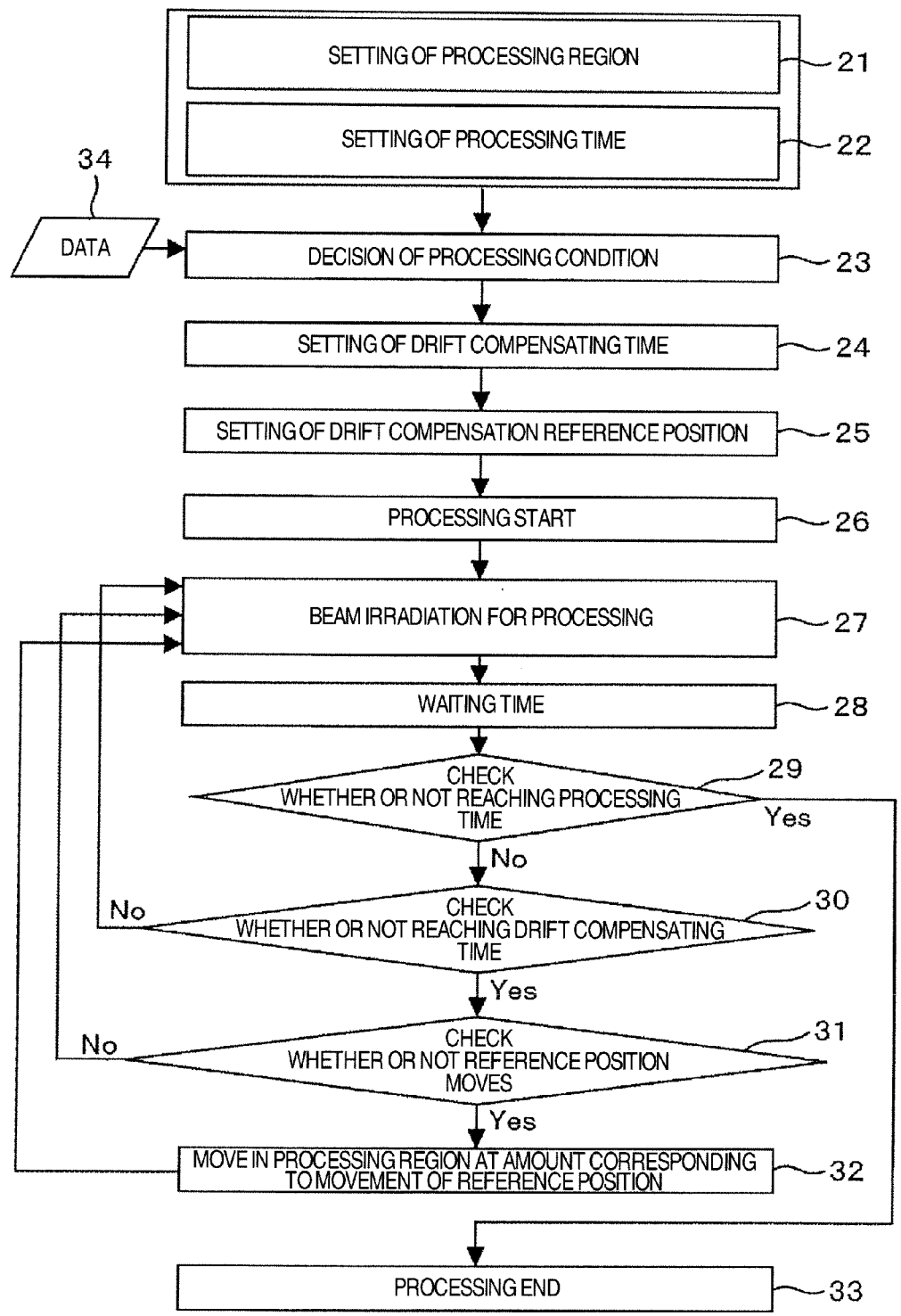
FIG. 3 is a flow chart of a cooling process by the charged particle.

In the processing provided with the waiting time, the following method is employed by taking a sample drift into consideration. In accordance with a flow chart shown in FIG. 3, a decision 23 of a processing condition is carried out by a setting 21 of a processing region, and a setting 22 of a processing time. A flow chart of the deciding work is shown in FIG. 2, and is structured such as to decide the unit beam irradiating time 19 of the charged particle, and the beam irradiation waiting time 20. At this time, if an already registered sample data 34 exists on an information system which can be referred from the device, it is possible to refer the sample data 34 so as to carry out the decision 23 of the processing condition without inputting a sample information each time. A setting 24 of a drift compensation time, and a setting 25 of a drift compensation reference position are carried out, and a processing start 26 is carried out. If the processing is started, a beam irradiation 27 for processing is carried out for a time corresponding to the unit beam irradiating time 19 which is conducted by the decision 23 of the processing condition. Next, a waiting time 28 till the next processing is provided. This waiting time is the beam irradiation waiting time 20 which is conducted by the decision 23 of the processing condition. If a total processing time goes beyond the setting 22 of the processing time by checking 29 whether or not it reaches the processing time, it is finished by a processing end 33. The processing is carried on while compensating the drift during the time. The drift compensation checks 30 whether or not a total elapsed time from a final drift compensation reaches the drift compensation time, and goes back to the beam irradiation 27 for processing if it does not reach. If it reaches, it checks 31 whether or not a reference position moves, and if it does not move, it goes back to the beam irradiation 27 for processing. If it moves, it moves 32 in a processing region at an amount corresponding to a movement of the reference position. Therefore, it goes back to the beam irradiation 27 for processing, and carries on series of processing.

FIG. 4 shows in detail a cooling holder in accordance with the present embodiment and a part of a sample stage of a charged particle device.

The cooling sample table 3 mounting the micro sample 1 thereon is set to a cooling gear A35. The cooling gear A35 is provided with a shaft on a cooling pipe 36. In this case, since a process till fixing the micro sample 1 to the cooling sample table 3 has already existed (refer to Ohnishi T., Kike H., Ishitani T., Tomimatsu S., Umemura K., and Kamino T., Proc. 25th Int. Symp. Test. And Fail. Anal. (1999) 449-453. (non-patent document 1)), the description thereof will be omitted here. In this case, the disclosed content of the non-patent document 1 constructs a part of the disclosed contents in the present specification. The cooling gear A35 is controlled its rotation by a cooling gear B38 which is provided in a leading end of the cooling shaft 37. The micro sample 1 is given a rotation by a vertical axis of a paper surface on the basis of a rotation of the cooling gear A35. In this case, the cooling shaft 37 is supported by thermal shield bearings 56 and 57 which are provided within a cooling pipe 36. The cooling sample table 3 can be optionally detached from the cooling gear A35 after the processing and observing are finished, and can be again set at an optional occasion so as to be processed and observed.

The micro sample 1 is connected to the cooling source via the cooling sample table 3, the cooling gear A35, the cooling gear B38, the cooing shaft 37, a cooling gear C39, a flexible heat conductor 40, a cooling rod 41 and a flexible heat conductor 42. Further, the micro sample 1 is connected to the cooling source via the cooling sample table 3, the cooling gear A35, the cooling pipe 36, the cooling rod 41 and the flexible heat conductor 42. The micro sample 1 is cooled to the vicinity of the temperature of the cooling source. On the basis of the structure mentioned above, all of the peripheral portion of the micro sample 1 comes to a cooled structure, and a sample cooling efficiency is high. In this case, the flexible heat conductor 40 may be structured such as to utilize a plastic deformation which is generated by a slip of an atomic level, or may be structured as a mechanical flexible heat conductor which utilizes a physical slip.

The cooling source is retained within a cooling source container inner side 44, and is isolated from an outer world by a cooling source container outer side 46 which is thermally isolated by a heat shield 45. A portion between the cooling source container inner side 44 and the cooling source container outer side 46 is vacuum, and this plays a role of holding the thermal isolation from the outer world.

The cooling gear C39 is provided in a terminal end portion of the cooling shaft 37, and is connected to a motor 51 via a heat shield gear A47, a gear 48, a shaft 49 and a gear box 50. On the basis of a motor rotation reading cable 53, a sample rotating angle is calculated by a motor controller which is not expressed in the drawing, and there is provided with a mechanism of applying an appropriate operation of the motor 51 from the motor controller via a motor power supply cable, in such a manner as to come to a target sample rotating angle.

A holder rotation part outer wall 54 inward enwraps the cooling shaft 37, the cooling pipe 36, the gear box 50, the motor 51 and the like, and is thermally isolated from the cooling pipe 36 by a heat shield 58, a heat shield 60, a heat shield 61 and a heat shield 62. The holder fixing part 55 further inward enwraps the holder rotation part outer wall 54 concentrically, and a movable heat shield 59 and an O-ring 65 are provided therebetween. A guide pin 72 is provided in the holder fixing part 55, and comes into contact with a device holder receiver 67 and a device holder receiver 68 via an O-ring 66. A positional relationship of the cooling holder 8 with respect to a whole device is based on the guide pin 72.

A lot of devices having different modes exist as a processing device and an observing device on the basis of the charged particle. For example, in the case of the transmission type electron microscope (TEM), there are an accelerating voltage 100 KV directed to a biological sample observation, an accelerating voltage 200 KV directed to a semiconductor device or a material, an accelerating voltage 300 KV directed to a high resolving power observation, and the like. One essential problem which makes unification of these electron microscopes hard is a difference in diameters of mirror bodies. Further, on the basis of the difference in the diameters of the mirror bodies, three kinds of devices mentioned above are different in a distance between the sample position and a stage which is attached to a device for controlling the sample position and the holder. The guide pin 72 is provided for deciding a positional relationship between the holder and the stage, and in the case that the observation is going to be carried out in all the devices by using one holder, it is necessary that the guide pin 72 can be changed its distance from a leading end in correspondence to the device. In the present embodiment, the guide pin 72 is structured such as to take thee positions for the accelerating voltages 100, 200 and 300 KV, while taking this matter into consideration.

The holder fixing part 55 takes a state of being set to the device. On the other hand, the holder rotation part outer wall 54 can rotate all the inward enwrapped materials in an optional direction on the basis of a rotation on a transverse axis of a paper surface, regardless of the holder fixing part 55. The holder rotation part outer wall 54 can be provided with a mechanism which electrically rotates on the basis of a motor drive which is not illustrated. In a movement between the different devices, the holder rotation part outer wall 54 is rotated in such a manner as to come to a sample direction which is perfect for the target device. The flexible heat conductor 42 is not affected by the rotation, but always connects thermally the cooling source 43 and the cooling rod 41.

Further, in order to avoid a sample breakage and soil during the conveyance in the movement between the devices, a shutter 70 is provided. The shutter 70 can be used at a position 70a within the device and at a position 70b during the conveyance. Further, the shutter 70 can be optionally actuated by a shutter operation portion 71 which is pulled out to an outer side, even during the processing or the observing. Further, the shutter operation portion 71 can be further connected to a known mechanical operation portion which is not illustrated, and can be changed to a motor drive.

A typical positional relationship between the device and the sample is shown by using FIG. 5. In FIG. 5, a vertical direction of a paper surface is a longitudinal direction of the cooling holder 8. Within the FIB device manufacturing the thin film sample, as shown in FIG. 5(a), the thin film sample is arranged in parallel to the charged particle A5 which is discharged from an FIB objective lens 73, and the thin film sample is manufactured while being cooled, by alternately processing a processing and observing surface A77 and a processing and observing surface B78.

Within an electron microscope which observes the manufactured thin film sample, as shown in FIG. 5(b), the thin film sample is arranged approximately vertically to the charged particle B6 (the electron beam in this case), and a sample observation is carried out in a cooled state, by using a transmitted wave 75 or the like. Further, the signal 7 (for example, a characteristic X ray) emitted from the sample passes through the space 4 which is not illustrated so as to be efficiently detected, and can be utilized for evaluating the sample. In this observation, in the sample having the crystal structure, it is necessary to rotate the sample incline to the vertical direction of the paper surface or the in-plane direction. As mentioned above, this purpose is easily achieved by the existence of the sample rotation mechanism.

In the device in which the FIB device and the electron microscope are conjugated, it is possible to observe the structure appearing on the processing surface while processing the sample. Particularly, in the case that it is desired to manufacture the thin film sample while leaving the sample having a special shape within the thin film at an accurate position in a thin film thickness direction, the conjugating device achieves its effectiveness. For example, in the case of forming a true cross section of a micro plug within a semiconductor device into a thin film, the conjugating device is used. In this conjugating device, the processing and observing surface A77 is observed by the charged particle B6 (the electron beam in this case) while being processed by the charged particle A5 (a focused ion beam in this case). In the case of forming the true cross section of the plug into the thin film, first of all, the processing and observing surface A 77 is observed while being processed, and the processing is carried on until the target plug is going to be seen, as shown in FIG. 5(*c*). If the plug is seen, the processing and observing surface B 78 is observed while being processed as shown in FIG. 5(*d*), and the processing is carried on until the target plug is going to be seen. The thin film sample is manufactured in such a manner that the plug diameters which are observed in the processing and observing surface A 77 and the processing and observing surface B 78 become equal, by repeating this step. As a result, if the conjugating device is used, it is possible to easily form the true cross section into the thin film in a state in which the target plug is accommodated within the thin film. In order to change the processing and observing surface A 77 and the processing and observing surface B 78 while cooling them within the device in the processing process mentioned above, the transverse rotation at 180 degree having the vertical direction of the paper surface as an axis is necessary, however, the present embodiment enables it.

In the case of in detail observing the manufactured thin film sample as it is in the cooling state, by the conjugating device mentioned above, it is desirable that the thin film sample is arranged vertically to the charged particle B 6 (the electron beam in this case) as shown in FIG. 5(*e*). In FIG. 5(*e*), an illustration of the FIB objective lens 73 and the charged particle A 5 is omitted. Further, the sample rotation in two axes is demanded for evaluating the crystal structure, however, the present embodiment can satisfy this purpose.

In the present embodiment, it is possible to directly fix the micro sample 1 to the detachable cooling sample table 3, and it is possible to carry out the processing and the observing while effectively cooling by one cooling holder.

Embodiment 2

Figure 6:
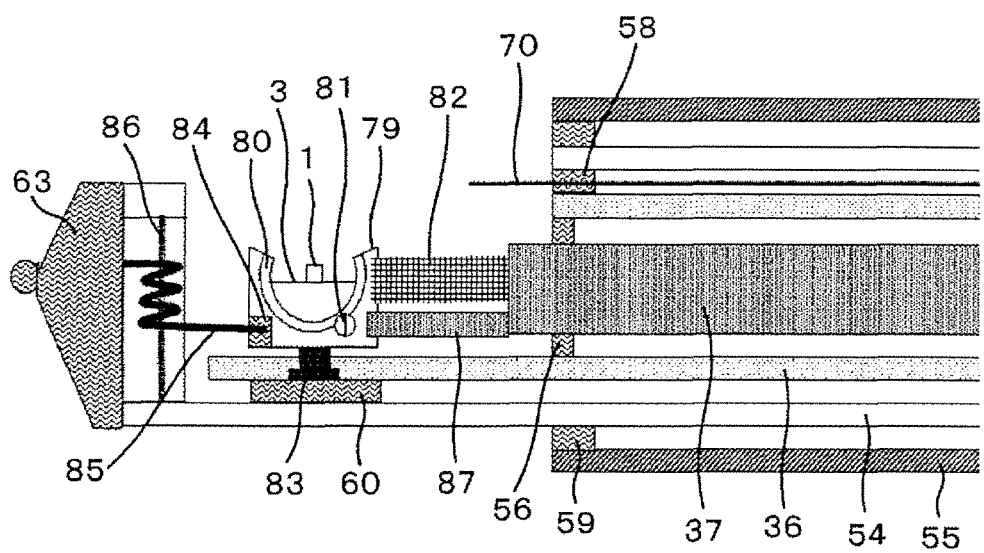
FIG. 6 shows a mesh corresponding biaxial inclined cooling holder.

FIG. 6 in detail shows a mesh corresponding biaxial inclined cooling holder in accordance with the present embodiment. Since the other structures than the leading end portion of the cooling holder are the same as the structured described in the embodiment 1, a description thereof will be omitted. Since a rough sample direction regulation going with the movement between the processing and observing devices is carried out by the same mechanism and method as the embodiment 1, a description thereof will be omitted. A description will be given below by focusing on a main different point from the embodiment 1.

The micro sample 1 is attached to the mesh type cooling sample table 3, and the cooling sample table 3 is further fixed to a cooling rotating table 79 by using a fixing plate 80 and a fixing screw 81. It is possible to easily detach or install the mesh type cooling sample table 3 from or to the cooling holder, by loosening or fastening the fixing screw 81.

The cooling rotating table 79 is thermally connected by the cooling shaft 37 and the flexible heat conductor 82. The micro sample 1 is thermally connected to the cooling source in the same manner as the embodiment 1 via the cooling sample table 3, the cooling rotating table 79, the flexible heat conductor 82, the cooling shaft 37 and the like, and is efficiently cooled. A temperature in a side of the device is shut off by a leading end heat shield 63, a heat shield 84, a heat shield 60, a movable heat shield 59 and the like, and is not conducted to the micro sample 1.

The cooling rotating table 79 is fixed to the cooling pipe 36 by a rotating shaft 83. A spring 85 presses the cooling rotating table 79 downward, and applies such a force as to rotate the cooling rotating table 79 on an axis in a vertical direction of the paper surface. On the other hand, a cooling rotating table pressing rod 87 which is fixed to the cooling shaft 37 applies such a force as to stop a rotating force which the spring 85 gives to the cooling rotating table 79. It is possible to change a position with respect to the rotating shaft 83 of the cooling rotating table pressing rod 87 by rotating the cooling shaft 37 by the motor 51 shown in the embodiment 1. It is possible to control an amount of rotation on the axis in the vertical direction of the paper surface of the micro sample 1, on the basis of the control of the cooling rotating table pressing rod 87. Since the amount of motor rotation and the amount of sample incline are decided on the basis of the structure of the rotation mechanism, it is possible to carry out a regulation of the amount of sample incline on the basis of an appropriate motor control by reading the amount of motor rotation. The rotation on the axis in the transverse axial direction of the paper surface can be carried out by the holder receiving stage in the side of the charged particle device in a whole of the cooling holder, and the holder rotation part outer wall 54 can be rotated by the motor drive.

In the present embodiment, it is possible to directly fix the micro sample 1 to the detachable cooling sample table 3, and it is possible to carry out the processing and the observing while effectively cooling by one cooling holder.

Embodiment 3

FIG. 7 shows a mesh corresponding uniaxial inclined cooling holder in accordance with the present embodiment. Since the other structures than the leading end portion of the cooling holder are the same as the structured described in the embodiment 1, a description thereof will be omitted. Since a rough sample direction regulation going with the movement between the processing device and the observing device is carried out by the same mechanism and method as the embodiment 1, a description thereof will be omitted. A description will be given below by focusing on a main different point from the embodiments 1 and 2.

The micro sample 1 is attached to the mesh type cooling sample table 3, and the cooling sample table 3 is further fixed to a cooling rotating table 79 by using a fixing plate 80 and a fixing screw 81. It is possible to easily detach or install the mesh type cooling sample table 3 from or to the cooling holder, by loosening or fastening the fixing screw 81.

The cooling rotating table 79 is connected to the cooling shaft 37. The micro sample 1 is thermally connected to the cooling source in the same manner as the embodiment 1 via the cooling sample table 3, the cooling rotating table 79, the cooling shaft 37 and the like, and is efficiently cooled. A leading end side of the cooling rotating table 79 is pressed in a heat shield 88 by a spring 89, and an oscillation during the observation of the cooling rotating table 79 is suppressed. A temperature in a side of the device is shut off by a leading end heat shield 63, a heat shield 84, a heat shield 60, a movable heat shield 59 and the like, and is not conducted to the micro sample 1.

The cooling rotating table 79 is given freely a rotation on the axis in the transverse direction of the paper surface on the basis of the rotation of the cooling shaft 37 by the motor drive. Further, the rotation can be applied by rotating a whole of the holder rotation part outer wall 54, and a whole of the cooling holder can be rotated on the axis in the transverse direction of the paper surface by an inclining mechanism of the holder receiving stage in a side of the device.

In the present embodiment, it is possible to directly fix the micro sample 1 to the detachable cooling sample table 3, and it is possible to carry out the processing and the observing while effectively cooling by one cooling holder. Further, the present embodiment is simpler in its structure in comparison with two embodiments mentioned above, however, a heat conducting characteristic is most excellent and a cooling efficiency is high. It is the cooling holder which is suitable for the sample in which the freedom of incline is allowed.

FIG. 7(b) is a structure in which the cooling efficiency is further enhanced. It is the structure in which the heat shield 88 of the cooing rotating table 79 is omitted, and the heat conduction from the leading end of the holder is completely shut off. This structure is effective in the case of placing an emphasis on the processing, and can process while efficiently cooling the sample. In the observation by the electron microscope or the like, the observation and the analysis are carried out within the range of the uniaxial incline.

Embodiment 4

A description will be given of a cooling processing method and a processing condition calculation in the present embodiment.

In the cooling processing by the charged particle, the processing region 10, the processing electric current 11, the processing accelerating voltage 12 and the like are set on the basis of the initial setting 9 of the processing condition in accordance with the flow chart in FIG. 2. Next, on the basis of the setting 13 of the sample condition, the coefficient of thermal conductivity 14 of the sample, the sample breaking temperature 15, the thermal emission rate 16, the outer portion cooling temperature 17 and the like are set. Further, the unit beam irradiating time 19 and the beam irradiation waiting time 20 are decided by carrying out the calculation 18 of an appropriate processing condition. The charged particle current amount, the irradiating time and the waiting time till the next irradiation are decided by taking into consideration the heat transfer characteristic of the sample, the sample aspect and/or the target cooling temperature by the means mentioned above, and the processing which does not prevent the cooling effect is carried out.

Figure 8:
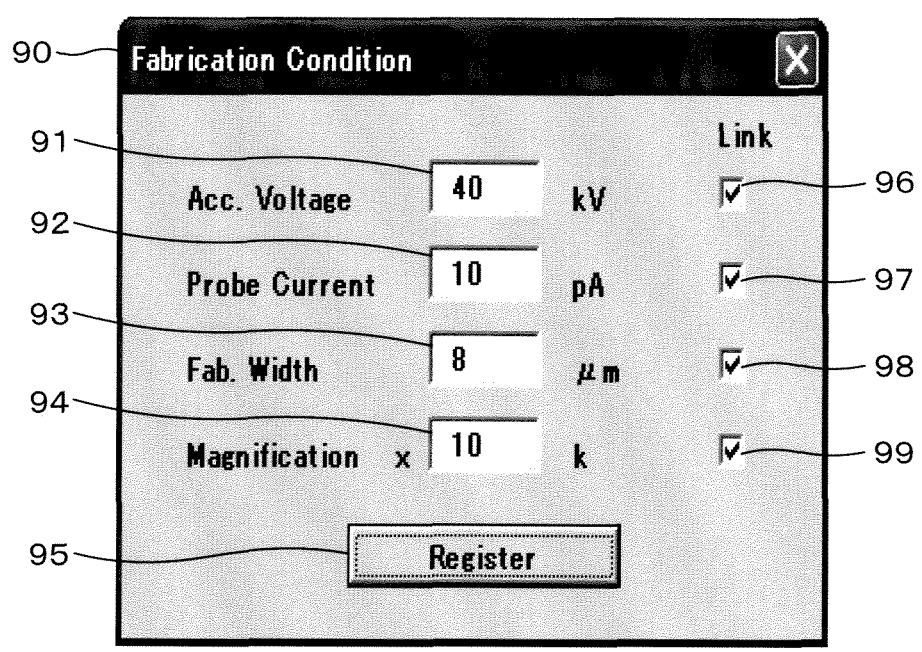
FIG. 8 shows a processing condition registration window.

FIG. 8 shows a processing condition initial input window 90. A condition is input by carrying out an accelerating voltage input 91, a probe electric current input 92, a processing width input 93, and a processing magnification input 94, and pushing a registering button 95. Since each of the conditions can be read as a digital information within the processing device, the present embodiment is provided with device link effectiveness checks 96, 97, 98 and 99, and has such a function that the information is automatically displayed. It is sufficient for an operator to check whether or not the display data is different from the condition under use.

Figure 9:
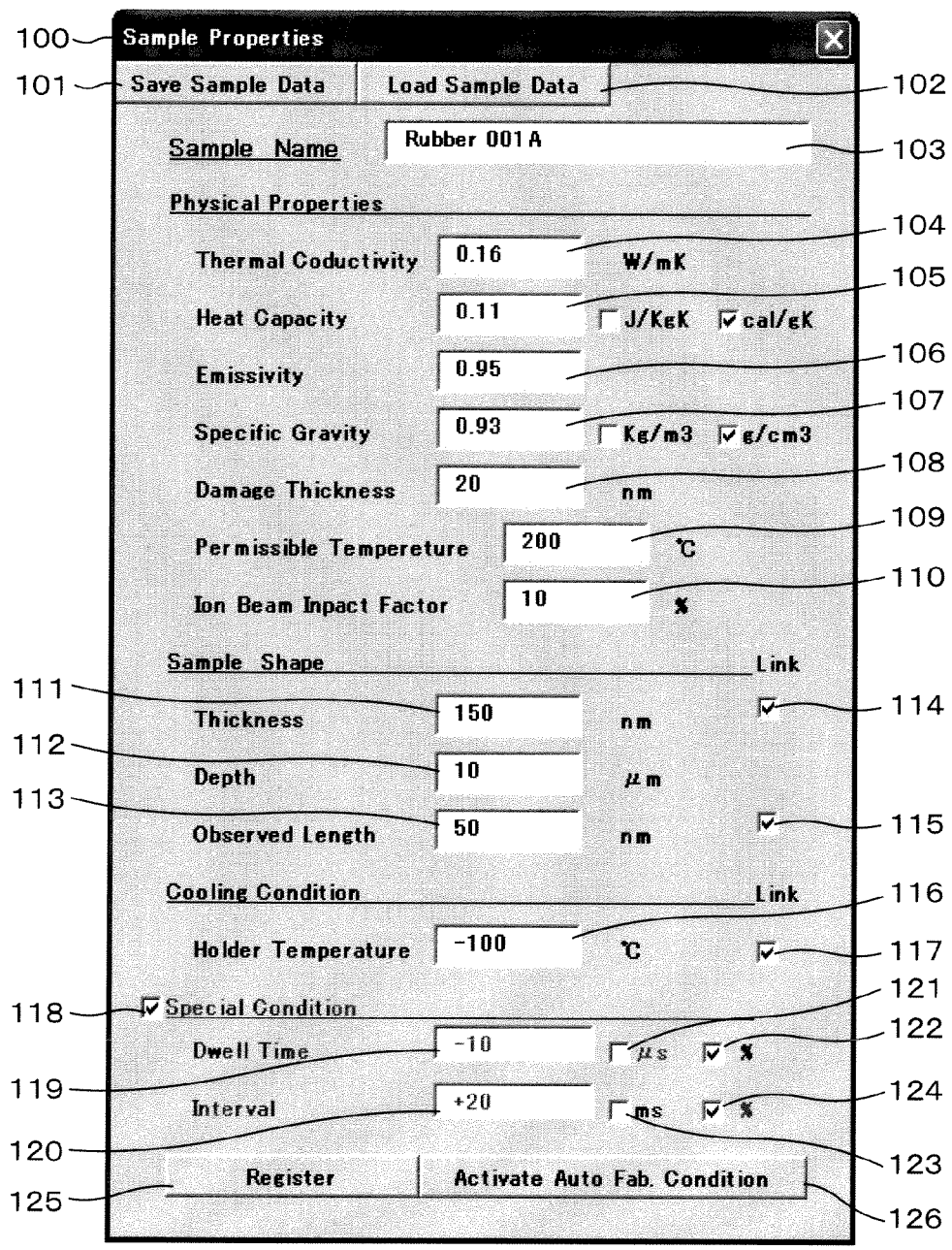
FIG. 9 shows a sample condition registration window.

FIG. 9 shows a sample information input window 100. In this window, the information relating to the sample is input mainly. The present embodiment is provided with a sample information save button 101, and a sample information load button 102, and it is possible to omit such a labor hour to input the sample information each time. A description will be given below of the input information. A sample name input 103, a coefficient of thermal conductivity input 104, a specific heat capacity input 105, an emissivity input 107, a specific gravity input 107, a thickness input 108 of a damage layer generated at a time of processing, an allowable temperature input 109 and an ion beam impact factor 110 relate to an original physical property of the sample, and are the information which can be used by loading the sample date every time as long as the sample is the same. In this case, a description about a general physical constant will be omitted. The thickness of the damage layer generated at a time of processing is a thickness of a layer which is different from the original state of the sample and is created on the processing surface by the FIB processing, and indicates a region of an amorphous material in Si. The allowable temperature is a temperature which the sample can change from the original state of the sample, and in the case that an ice crystal is intended to be formed as a thin film, 0° C. or less is the allowable temperature. The ion beam impact factor indicates a rate of an energy which is not used as an energy for shaving the sample by sputtering in the input energy, but contributes to a temperature rise of the sample, for example, by an ion implantation or the like. In the case of the sample in which the experimental data is obtained, its value is input, however, since an actually measured value is little in the present circumstances, a calculating method using a Monte Carlo simulation comes to an immediate calculating method. "The Stopping and Range of Ions in Matter (non-patent document 2)" by James F. Ziegler exists as a typical one of the Monte Carlo simulation method which calculates an ion behavior at a time when the ion beam is irradiated on the sample. Since details of the Monte Carlo simulation does not directly relate to the present embodiment, a description thereof will be omitted. In this case, the disclosed contents of the non-patent document 2 constructs a part of the disclosed contents in the present specification.

In the sample information input window 100, there are a sample thickness input 111, a size input 112 in a processing depth direction of the sample, and an observing width input 113 in the processing device of the processing surface, as an input of the sample shape. The sample thickness is a thickness of the thin film, and indicates a thin film thickness 138 of the thin film processing region shown in FIG. 11(b). The size in the processing depth direction of the sample is a height of the micro sample 1 shown in FIG. 11(b), and is necessary to be measured at a time of attaching the micro sample 1 to the cooling sample table 3. However, since it is a value which does not change by the processing, it is sufficient to input once. Viewing the cross section of the thin film shown in FIG. 11(b) from the transverse direction in the thin film processing, it normally comes to such a shape as shown in FIG. 11(c), and the observing width in the processing device of the processing surface indicates a width 139 at a time of viewing a slope of the processing surface directly from the above (the observing direction during the processing in the FIB device). The thin film thickness 138 and the observing width 139 of the thin film sample processing surface always change during the processing, and a recalculation of he input and the condition are necessary each time, however, this is provided with the device link effectiveness checks 114 and 115, and has such a function as to transfer the information from the processing image display screen in the side of the device. The processing screen indicates FIG. 11(a), and is automatically measured by aligning with the processing surface and the thin film portion on he screen of the scanning ion microscope (SIM) image in which an observing width measurement frame 135 of the thin film sample processing surface, and a thin film thickness measurement frame 136 are observed, and results are transferred to the sample thickness input 111, and the observing width input 113 in the processing device of the processing surface. Further, as a device link relating to the thin film thickness, for example, in the case that the FIB device, the SEM and the STEM device are conjugated, it is possible to transfer a thin film thickness measurement information which is obtained by analyzing a signal obtained from the sample in the side of the SEM or the STEM device. In this case, the thin film thickness measurement by the SEM or the STEM device indicates a method which utilizes a reflected electron, a method which utilizes an elevation angle scattered wave in a transmission side, and a method which utilizes an electron energy loss spectral method (EELS). Since they are the existing techniques, a detailed description will be omitted.

In the sample information input window 100, a sample cooling temperature by the cooling holder is input by the cooling temperature input 116. In this case, a holder cooling temperature which is measured in a thermo couple (which is not shown in FIG. 4) by the device link effectiveness check 117 is transferred.

The sample information input window 100 further has such a function as to carry out a processing condition compensation on the basis of an experience while taking into consideration the case of a complicated sample aspect. Specifically, a special condition effectiveness check 118 is provided, and it is possible to compensate a calculated unit ion beam irradiating time 128 and a beam irradiation waiting time 129 by a unit ion beam irradiating time regulating amount 119 and a beam irradiation waiting time regulating amount 120. The input may be set per each of units, and may be set by a rate with respect to the calculated results.

The calculation of the condition is carried out by inputting the necessary information and pushing the decision button 125. The condition calculation in the present embodiment is carried out about such a unit ion beam irradiating time 128 that the temperature rise given to the sample processing surface of the unit ion beam irradiation does not affect the sample, and such a beam irradiation waiting time 129 as to take into consideration a time until the heat amount given by the unit ion irradiation is sufficiently transmitted to the cooling portion by the next unit irradiation.

The calculating method is shown below. The sample allowable temperature is set to MT, the sample cooling temperature is set to Tg, and the amount at which the temperature of the sample surface rises by the unit ion beam irradiation is set to dT. In the present embodiment, dT is set as the following condition.

$$dT = (MT - Tg)/3 \quad (1)$$

Since various cases can be thought as this setting condition, a description of all will be omitted. Next, an energy J which the unit ion beam irradiation gives as a temperature to the sample is indicated as follows by using the input information mentioned above.

$$J = A \cdot t \cdot V \cdot Ef \quad (2)$$

In this case, a probe electric current is set to A, a beam irradiating time is set to t, a processing accelerating voltage is set to V, and an ion beam impact factor is set to Ef. The following relationship is established between the energy J which the ion irradiation gives to the sample, and the processing surface temperature dT which instantaneously rises by the ion irradiation.

$$dT = J/(g \cdot C) \quad (3)$$

In this case, g is a mass of the processing surface. In the present embodiment, a thickness about a damage layer is assumed to be a region which the ion beam instantaneously affects, and a mass corresponding to the damage layer is assumed to be a mass of the processing surface. Further, C is a specific heat. On the basis of the expressions (1), (2) and (3), the beam irradiation time t is shown as follows.

$$t = (dT \cdot g \cdot C)/(A \cdot V \cdot Ef) \quad (4)$$

The FIB processing device processes in accordance with a method of processing by making the beam stay per 1 pixel of the processing screen, and the time is generally called as Dwell Time. On the basis of the magnification input information mentioned above, a correspondence between 1 pixel in the process under processing and an actual distance can be easily obtained. In the condition calculation, the Dwell Time, that is, the unit ion beam irradiating time in the present embodiment is determined by once determining the region which the beam in the pixel unit irradiates, and carrying out the calculation mentioned above about the portion.

On the other hand, in the beam irradiation waiting time, the time until the heat energy applied by the unit ion beam irradiation is reduced to a steady state is determined. As a model, there is thought a case that the ion beam goes on being irradiated on the thin film at a certain time interval. After a certain fixed time, an average sample temperature becomes constant, and a stationary heat flow heading for the cooling portion is expected to be generated. The heat flow rate Q at this time is shown by the following expression.

$$Q = -\lambda \text{grad} T \cdot S \quad (5)$$

In this case, $\lambda$ is a coefficient of thermal conductivity, T is a temperature, gradT is a temperature gradient, and S is a cross sectional area by which the thin film comes into contact with the portion which is sufficiently cooled and is not processed. The temperature gradient is shown in a simple manner by the following expression by using an average sample temperature Ts, a cooling temperature Tg and a thin film width W.

$$\text{grad} T = 2 \cdot (Ts - Tg)/W \quad (6)$$

In the case that the calculation is carried out in more detail, an x coordinate is provided in a thin film width direction, and a temperature distribution simulation is carried out. Generally, in such a model that both ends of the thin film come into contact with the cooling portion, and a uniform heat is applied to a whole, there is obtained a distribution in which the temperature is higher at the center so as to be arched, and drops in both ends. Both are the parameter which can be calculated from the input information.

Further, the following relationship is established between the heat energy J applied by the unit ion beam irradiation and the flowing out heat flow rate Q.

$$J = Q \cdot tw \quad (7)$$

In this case, tw is a reducing time, and corresponds to a necessary beam irradiation waiting time.

On the other hand, the heat flowing out of the sample includes a radiation heat R which has a small contribution, in addition to a heat conduction. The radiation heat R radiates the following heat per unit time.

$$R = 2 \cdot \sigma \cdot \epsilon \cdot S_{surface} \cdot (Ts^4 - Ta^4) \quad (8)$$

In this case, $\sigma$ is a Stefan-Boltzmann constant and has a value of $5.67 \times 10^{-8}$ [$Wm^{-2}K^{-4}$]. $\epsilon$ is an emissivity of the sample. $S_{surface}$ is a surface area of the thin film, and is an area contributing to the radiation. It is nearly similar to the thin film area in the case of the thin film. Ta is a surface temperature of a material surrounding the sample. Taking the radiation heat R into consideration, the expression (7) comes to as follows.

$$J = (Q + R) \cdot tw \quad (9)$$

Accordingly, it is shown by the following expression.

$$tw = J/[\lambda \text{grad} T \cdot S + 2 \cdot \sigma \cdot \epsilon \cdot S_{surface} \cdot (Ts^4 - Ta^4)] \quad (10)$$

In the present embodiment, the sample temperature Ts is set as follows in order to prevent the instantaneous temperature from going beyond the allowable temperature on the basis of the average sample temperature.

$$Ts = (MT - Tg)/6 + Tg \quad (11)$$

However, this is first and foremost one example setting, and various setting methods can be thought.

Figure 10:
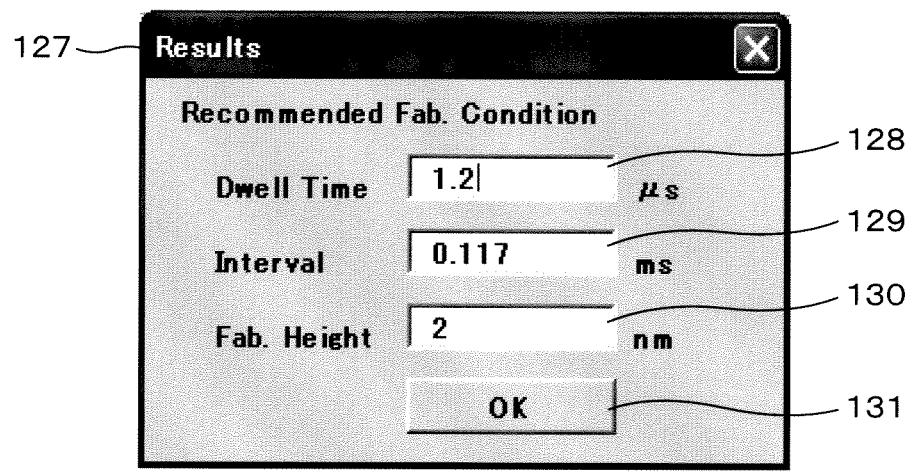
FIG. 10 shows an appropriate processing condition calculation result display window.

The unit ion beam irradiating time 128 and the beam irradiation waiting time 129 are respectively calculated as 1.2 μs and 0.117 ms, on the basis of the input mentioned above and the calculation mentioned above. Results are displayed on a condition calculation result window 127 as shown in FIG. 10. A condition registering button 131 is a button for registering after checking the condition. At a time of registering, an operator can slightly correct each of the values from the calculated values so as to register. Further, as a preparative calculation, a height 130 of such a processing area as to come back to the same processing pixel just after an elapse of the beam irradiation waiting time by the calculated unit ion beam irradiating time and processing width is also calculated for reference. In the case that the set processing region is larger than the height originally, the waiting time until the next processing beam is irradiated to each of the processing pixels goes beyond the necessary waiting time. Accordingly, it is possible to carry out the processing as it is. On the other hand, in the case that the height of the primarily set processing area is smaller than the suggested height, it is necessary to widen the processing region to this height or enter into the next processing scan after waiting a necessary time after processing and scanning the set region. The present embodiment can correspond to both of them, and if the operator freely set the processing region, the irradiation of the ion beam is carried out under the condition which is required by the device side.

Further, if a processing condition automatic regulation effective button 126 is pushed in the sample information input window 100, all the link function becomes effective. If the processing region is set on the screen, and the processing is started, the condition is automatically calculated, and the processing is started by the appropriate unit ion beam irradiating time 128 and beam irradiation waiting time 129.

If the sample condition of the cooling processing is once registered at the beginning in accordance with the present embodiment, it is possible to freely set the processing region, and there is achieved a cooling charged particle processing device in which the device determines the detailed parameters and the irradiating procedures.

In a state in which the thin film thickness becomes thinner to 50 nm, the incline of the sample processing slope is increased, and the observing width in the processing device of the processing surface is increased to 150 nm, the result of calculation under the same condition comes to DT=0.4 μs, and Interval=0.35 ms. Since the suggested processing width is 15 nm, and is narrower than the normal processing region, the processing is carried out as it is in the normal setting region.

Embodiment 5

A description will be given of a cooling processing method in accordance with the present embodiment.

In order to obtain an effect of reducing a temperature rise by the ion beam processing without cooling the sample, a very small amount of irradiation and irradiation waiting time which are hard to be realized are necessary. The processing while cooling is an effective means for realizing the effect for as short as possible irradiation waiting time. However, in the cooing processing, since the amount of irradiation of the charged particle and the frequency of irradiation become low as described in the embodiment 4, a total time demanded for processing becomes longer in comparison with the normal ion beam processing in which it is not necessary to take into consideration the sample temperature rise by the ion beam.

During this long processing time, the sample brings on a drift, and the processing region moves. In the present embodiment, the following method is employed while taking the sample drift into consideration. In accordance with a flow chart shown in FIG. 3, a processing region setting 21, a processing time setting 22 and a processing condition decision 23 are carried out. The flow chart of the deciding work is that shown in FIG. 2, and decides the unit beam irradiating time 19 of the charged particle, and the beam irradiation waiting time 20. At this time, if the already registered sample data 34 exists on the information system which can be referred from the device, it is possible to refer the sample data 34 so as to carry out the decision 23 of the processing condition without inputting the sample information each time. Since the details are described in the embodiment 4, the description will be omitted here.

A drift compensating time setting 24 and a drift compensation reference position setting 25 are carried out, and a processing start 26 is carried out. If the processing is started, a beam irradiation 27 for processing is carried out for a time corresponding to the unit beam irradiating time 19 which is conducted by the processing condition decision 23. Next, a waiting time 28 till the next processing is provided. The waiting time is the beam irradiation waiting time 20 which is conducted by the processing condition decision 23. If the total processing time goes beyond the processing time setting 23 by checking 29 whether or not it reaches the processing time, the processing is finished in accordance with a processing end 33. Until that moment, the processing is carried on while compensating the drift. The drift compensation carries out a checking 30 whether or not the total elapsed time from the final drift compensation reaches the drift compensating time, and goes back to the beam irradiation 27 for processing if it does not reach. If it reaches, it carries out a checking 31 that the reference position does not move, and if it does not move, it goes back to the beam irradiation 27 for processing. If it moves, it moves 32 in the processing region at an amount corresponding to the movement of the reference position. Thereafter, it goes back to the beam irradiation 27 for processing, and a series of processing is carried on.

Figure 12:
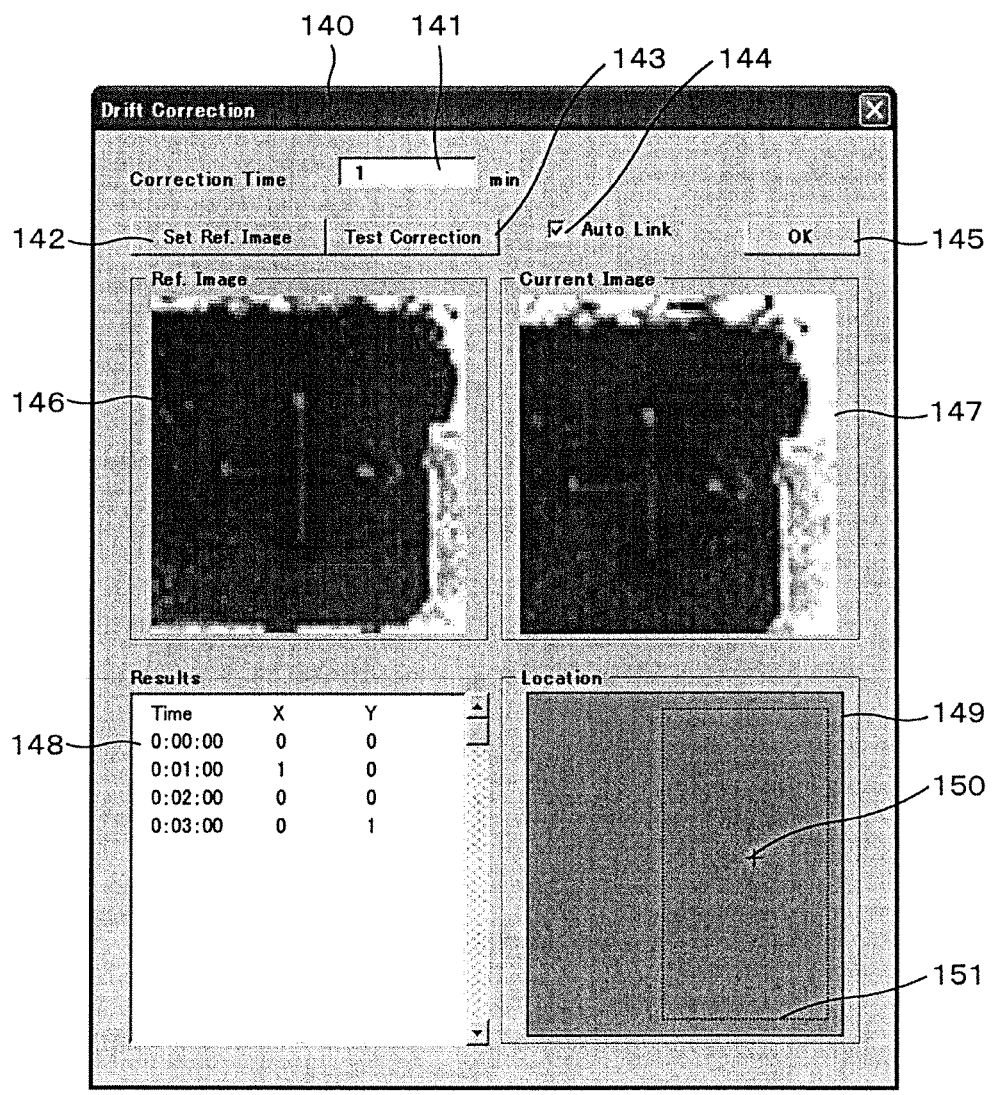
FIG. 12 shows a drift compensation window.

FIG. 12 shows a drift compensation window. The drift compensation window 140 is a window for setting an optional position as a drift compensation reference area on a charged particle scanning screen by a drift compensating time 141 and a drift compensation reference area setting button 142, and setting the drift compensation for an optional time. In order to check whether or not the set reference point is effective, a drift test button 143 is provided. This function is a function of making the scanning of the charged particle displace at a certain fixed amount in x and y directions and checking whether or not the same value as the set displacement or the vicinity value can be detected. As a result of test, a result evaluating the drift is displayed in a drift evaluation result 148 by using the given displacement and the set reference point. The operator of the device determines whether or not the result is in a compromised range, and pushes a settlement button 145 if it is in the range. Normally, under manufacturing of one thin film sample, the same drift compensation reference area is used, and the processing position, the processing shape and the processing time are changed. Since it is not necessary to carry out various settings and check whether or not the compensating position functions normally, by opening the drift compensation window 140 each time, at a time of changing the processing position, the processing shape and the like, the drift compensation reference area link button 144 is provided. By making the button effective, the position of the drift compensation reference area 158 (refer to FIG. 11) in the side of the device is registered as it is as the drift compensation reference position only by moving the position of the drift compensation reference area 158 to an appropriate place to be set as the compensation reference area, at a time of changing the processing area 132, and it is possible to start the cooling processing of the state in which the drift compensating function is effective. If all the device link functions of the embodiment 4 and the embodiment 5 are made effective, the operator can easily carry out the charged particle processing carrying out the drift compensation under the processing condition which does not prevent the cooling effect, only by regulating the processing area 132, the processing time 22, the drift compensation reference area 158, the thin film thickness measuring frame 136 and the observing width measuring frame 135 of the thin film sample processing surface on the device screen. During the drift compensation, a reference image 146 and a current image 147 evaluating the drift are displayed on the drift compensation window 140. The result of compensation is displayed in the drift evaluation result 148 together with the time carrying out the compensating process each time. A place display 149 shows what position the drift compensation reference area exists in the charged particle screen, by a present compensation reference position 150. A compensation reference position limit display 151 shows a position of the compensation reference area at which a part of the compensation area or a part of the processing area after compensating jumps out of the charged particle screen. Since the compensated image can not acquired in the case that the compensation reference position jumps out of the screen, the drift compensation can not be carried out. Further, in the case that the processing area after compensating jumps out of the screen, the processing can not be carried out. The processing is finished at a time when the present compensation reference position 150 comes out of the compensation reference position limit display 151.

Embodiment 6

Figure 13:
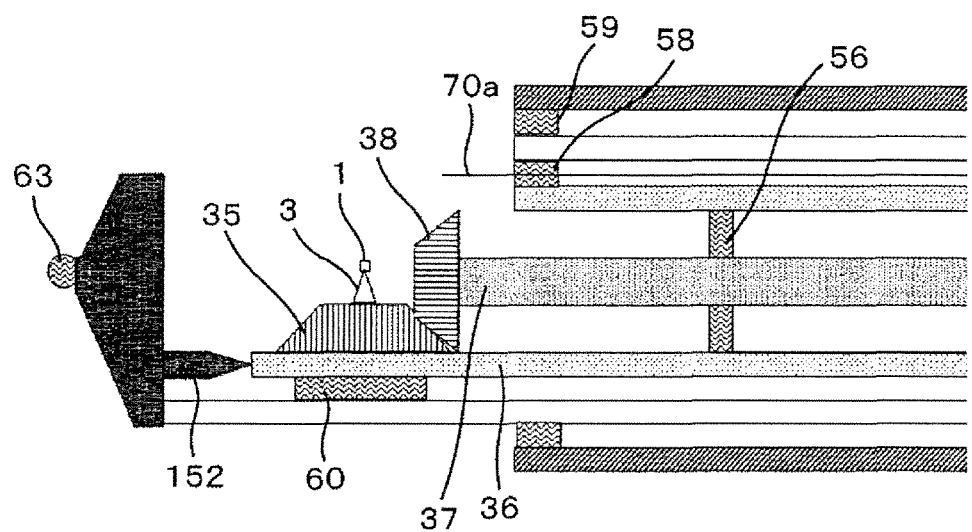
FIG. 13 shows a dew condensation preventing type cooling holder.

FIG. 14 shows a dew condensation preventing type cooling holder in accordance with the present embodiment. Generally, in the charged particle processing device as represented by the FIGURE device, there is not equipped with a cold finger which adsorbs a contamination material in the vicinity of the sample within the device cooled to the temperature in the vicinity of a liquid nitrogen temperature, and a material which is coagulated by being cooled. If the cooling holder is used within the device mentioned above, the contamination or the dew condensation is generated by a degree of vacuum within the device and an amount of water vapor included in the vacuum, and the coagulated material is attached to the surface of the sample. The present embodiment solves this problem. Since the base structure of the cooling holder is obtained by setting a micro heat transfer material 152 in a leading end portion of any type of the embodiment 1, the embodiment 2 and the embodiment 3, a description of a whole of the holder is omitted here. FIG. 13 shows an example in which a dew condensation preventing mechanism is provided in the cooling holder in accordance with the embodiment 1.

The micro heat transfer material 152 is provided in the cooling sample table 3 to which the micro sample 1 is attached, and the cooling gear A35 to which it is set, in a different direction from the cooling gear B38, the cooling shaft 37 and the cooling pipe 36 which give the cooling effect. In accordance with this structure, a temperature gradient is generated around the sample. The temperature gradient comes to such a gradient that a temperature in the side of the micro heat transfer material 152 is higher and a temperature in the side of the cooling source is lower. In accordance with this structure, the cooling shaft 37 in FIG. 13 comes to a temperature which is sufficiently lower than the sample, and plays a part of coagulating and adsorbing the contamination material and the water vapor in the vicinity of the sample, substantially such as the cold finger. The micro heat transfer material 152 may be formed such as a needle or may be formed such as a leading end of a screw. The structure shown in FIG. 13 regulates the temperature gradient in the vicinity of the sample, by utilizing a phenomenon that the device is under about room temperature and the heat is conducted at a certain degree from the device to the micro heat transfer material 152 via the leading end heat shield 63. However, in the case that the temperature gradient which is suitable for the device can not be obtained only by the heat conduction via the leading end heat shield 63, the micro heat transfer material 152 may be heated a little by a heater which is not illustrated.

Embodiment 7

FIG. 14 shows a cooling holder in accordance with the present embodiment. Since the reference structure is the same as the embodiment 1, a description of the same portion will be omitted. The present embodiment achieves the portion which conducts the rotation of the cooling shaft 37 to the sample, by engaging the cooling gear A35 and the cooling gear B38 at an angle of 90 degree, on the basis of a different structure, for applying the rotation on the axis in the vertical direction of the paper surface of the sample in the embodiment 1.

The cooling sample table 3 is set to a cooling gear 157, and can be optionally detached from the cooling gear 157. The cooling gear 157 is structured such that a force is applied in a transverse direction of the paper surface by a rod-like cooling gear 156 which comes into contact with a side surface thereof, and the sample is rotated on an axial in a vertical direction of the paper surface. The cooling gear 156 is connected to the cooling rod 153, and the cooling rod 153 is further connected to the cooling gear 154. On the basis of the rotation of the heat shield gear 155 engaged with the cooling gear 154, the positions of the cooling rod 153 and the cooling gear 156 are changed. On the basis of the mechanism mentioned above, the heat shield gear 155 is moved by an electrically controlled motor, and it is possible to apply a rotation on an axis in a vertical direction of the paper surface to the sample which is positioned in the leading end portion of the holder. In order to conduct the heat of the cooling source 43 to the sample in this structure, the flexible heat conductor 42, the cooling rod 41, and the flexible conductor 40 are provided, as described in the embodiment 1. A different point from the embodiment 1 is a point that the flexible heat conductor 40 has the freedom of rotating on the axis in the transverse direction of the paper surface in the embodiment 1, however, it has a freedom of changing a length in a transverse direction of the paper surface in the present embodiment.

INDUSTRIAL APPLICABILITY

Since it is possible to efficiently cool the micro sample, a wide application in the material analyzing field can be expected. Since it is possible to freely incline the micro sample, it is possible to realize the processing and the detailed aspect observation of the micro sample without any heat damage. Further, the series of works from the cooling processing to the observing can be all executed by one holder, it is possible to widely shorten the working time from the processing to the observing. It is thought that a rapid development is applied to the material analysis and research.

DESCRIPTION OF REFERENCE NUMERALS 1 micro sample (sample)
2 processing and observing region
3 cooling sample table
4 space
5 charged particle A
6 charged particle B
7 signal emitted from sample
8 cooling holder
9 initial setting of processing condition
10, 21 setting of processing region
11 setting of processing current
12 setting of processing accelerating voltage
13 setting of sample condition
14 coefficient of thermal conductivity
15 sample breakage temperature
16 heat emission rate
17 outer cooling temperature
18 calculation of processing condition
19 unit beam irradiating time
20, 129 beam irradiation waiting time
22 setting of processing time
23 decision of processing condition
24 setting of drift compensating time
25 setting of drift compensation reference position
26 processing start
27 beam irradiation for processing
28 waiting time
29 check whether or not it reaches processing time
30 check whether or not it reaches drift compensating time
31 check whether or not reference position moves
32 move in processing region at amount corresponding to movement of reference position
33 processing end
34 sample data
35 cooling gear A
36 cooling pipe
37 cooling shaft
38 cooling gear B
39 cooling gear C
40, 42, 82 flexible heat conductor
41 cooling rod
43 cooling source
44 cooling source container inner side
45, 58, 60, 61, 62, 84, 88 heat shield
46 cooling source container outer side
47 heat shield gear A
48 gear
49 shaft
50 gear box
51 motor
52 motor power supply cable
53 motor rotation reading cable
54 holder rotation part outer wall
55 holder fixing part
56, 57 heat shield bearing
59 movable heat shield
63 leading end heat shield
64, 65, 66 O-ring
67, 68 device holder receiver
69 device holder receiver leading end side
70 shutter
71 shutter operation portion
72 guide pin
73 FIB objective lens
74 electron microscope in-lens type objective lens
75 transmitted wave
76 electron microscope objective lens
77 processing and observing surface A
78 processing and observing surface B
79 cooling rotating table
80 fixing plate
81 fixing screw
83 rotating shaft
85, 89 spring
86 spring fixing rod
87 cooling rotating table pressing rod
90 processing condition initial input window
91 accelerating voltage input
92 probe electric current input
93 processing width input
94 processing magnification input
95 registering button
96, 97, 98, 99, 114, 115, 117 device link effectiveness check
100 sample information input window
101 sample information save button
102 sample information load button
103 sample name input
104 coefficient of thermal conductivity input
105 specific heat capacity input
106 emissivity input
107 specific gravity input
108 thickness of damage layer generated at a time of processing input
109 allowable temperature input
110 ion beam shock coefficient input
111 sample thickness input
112 size in processing depth direction of sample input
113 observing width in processing device of processing surface input
116 cooling temperature input
118 special condition effectiveness check
119 unit ion beam irradiating time regulating amount
120 beam irradiation waiting time regulating amount
121, 122, 123, 124 unit selection check
125 deciding button
126 processing condition automatic regulation effectiveness button
127 condition calculation result window
128 unit ion beam irradiating time
130 height of processing area
131 condition registering button
132 processing area
133 processing width
134 processing height
135 observing width measuring frame of thin film sample processing surface
136 thin film thickness measuring frame
137 size in processing depth direction of sample
138 thin film thickness
139 observing width of thin film sample processing surface
140 drift compensating window
141 drift compensating time
142 drift compensation reference area setting button
143 drift test button
144 drift compensation reference area device link button
145 settlement button
146 reference image
147 current image evaluating drift
148 drift evaluation result 149 place display
150 present compensation reference position
151 compensation reference position limit display
152 micro heat transfer material
153 cooling rod
154, 156 cooling gear
155 heat shield gear
157 cooling gear
158 drift compensation reference area

The invention claimed is:

1. A sample holder comprising:
a sample table to which a sample piece picked out of a sample for an ion beam irradiation can be fixed,
a rotation mechanism which rotates said sample table in a desired direction along two axes perpendicular to one another, and
a cooling source for cooling said sample table, wherein:
the sample holder is structurally configured to be installed to both of an ion beam device and a transmission electron microscope,
the sample holder includes a movable first heat transfer material which thermally connects said sample table to the cooling source and a second heat transfer material which conducts heat in a direction different from a cooling source side, which provides a temperature gradient in the vicinity of the sample such that a portion of the second heat transfer material that is farthest from the sample has a higher temperature than a portion of the second heat transfer material that is closest to the sample and wherein the portion of the second heat transfer material that is closest to the sample has a temperature lower than that of the sample, and
said sample table and said first heat transfer material are further configured to be thermally isolated and enclosed within the sample holder by a removable shutter member.

2. The sample holder as claimed in claim 1, wherein said movable heat transfer material is a material or a structure which transfers heat by utilizing an atomic slip phenomenon including a plastic deformation, or utilizing a slip between materials.

3. The sample holder as claimed in claim 1, wherein said movable heat transfer material rotates on an axial direction in a longitudinal direction of the sample holder.

4. The sample holder as claimed in claim 1, wherein said movable heat transfer material is configured to extend and contract longitudinal direction of the sample holder.

5. The sample holder as claimed in claim 1, wherein a direction of said sample piece is rotatable at 180 degrees on an axis of a longitudinal direction of the sample holder.

6. The sample holder as claimed in claim 1, wherein:
the second heat transfer material includes any one of a tungsten, a molybdenum and a tantalum, and
the material or mechanism is configured to electrically control a temperature gradient.

7. The sample holder as claimed in claim 1, wherein the sample holder has a cover which is movable from an outer portion of the device for protecting the sample piece at a time of moving between charged particle devices.

8. A charged particle device including a sample holder comprising:
a sample table to which a sample piece picked out of a sample for an ion beam irradiation can be fixed,
a rotation mechanism which rotates said sample table in a desired direction along two axes perpendicular to one another, and
a cooling source for cooling said sample table, wherein:
the sample holder is structurally configured to be installed to both of an ion beam device and a transmission electron microscope,
the sample holder includes a movable first heat transfer material which thermally connects said sample table to the cooling source and a second heat transfer material which conducts heat in a direction different from a cooling source side, which provides a temperature gradient in the vicinity of the sample such that a portion of the second heat transfer material that is farthest from the sample has a higher temperature than a portion of the second heat transfer material that is closest to the sample and wherein the portion of the second heat transfer material that is closest to the sample has a temperature lower than that of the sample, and
said sample table and said first heat transfer material are further configured to be thermally isolated and enclosed within the sample holder by a removable shutter member, and
the charged particle device is configured to set a unit time for irradiating a charged particle beam and a waiting time until irradiating the charged particle beam to an identical position at a subsequent irradiation on the basis of: a coefficient of thermal conductivity of said sample, a specific heat, an emissivity, a specific gravity, an allowable temperature at which the sample piece is thermally stable, an interaction characteristic with the charged particle, a shape of the sample piece, an accelerating voltage of the charged particle device, a probe electric current, an observing region, a processing region, a processing magnification, an observing magnification and/or a sample cooling temperature.

9. The charged particle device as claimed in claim 8, wherein said unit time and said waiting time are automatically calculated on the basis of the coefficient of thermal conductivity of the sample, the specific heat, the emissivity, the specific gravity, the allowable temperature at which the sample piece is thermally stable, the interaction characteristic with the charged particle, the shape of the sample piece, the accelerating voltage of the charged particle device, the probe electric current, the observing region, the processing region, the processing magnification, the observing magnification and/or the sample cooling temperature.

10. The charged particle device as claimed in claim 8, wherein the information of the accelerating voltage of the charged particle device, the probe electric current, the observing region, the processing region, the processing magnification, the observing magnification and/or the sample cooling temperature is taken in, a calculation of the processing condition and the observing condition is carried out, and the processing and the observing are carried out under said condition.

11. The charged particle device as claimed in claim 8, wherein the coefficient of thermal conductivity of said sample, the specific heat, the emissivity, the specific gravity, the allowable temperature at which the sample piece is thermally stable, and/or the interaction characteristic with the charged particle are reserved as a physical property data of the sample piece, and are read in as occasion demands.

12. The charged particle device as claimed in claim 8, wherein a movement by a drift of said sample piece is detected and a processing position is compensated, at a time of accurately processing a desired position of said sample piece.

* * * * *